(12) United States Patent
Nishiyama et al.

(10) Patent No.: US 11,090,009 B2
(45) Date of Patent: Aug. 17, 2021

(54) INFORMATION PROVIDING METHOD, INFORMATION PROCESSING SYSTEM, INFORMATION TERMINAL, AND INFORMATION PROCESSING METHOD

(71) Applicant: Panasonic Intellectual Property Management Co., Ltd., Osaka (JP)

(72) Inventors: Yukari Nishiyama, Tokyo (JP); Masahiko Tsukuda, Osaka (JP); Yasuaki Okumura, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 142 days.

(21) Appl. No.: 16/577,764

(22) Filed: Sep. 20, 2019

(65) Prior Publication Data

US 2020/0008754 A1     Jan. 9, 2020

Related U.S. Application Data

(63) Continuation of application No. PCT/JP2018/021456, filed on Jun. 5, 2018.

(30) Foreign Application Priority Data

Jul. 7, 2017   (JP) .............................. JP2017-133368

(51) Int. Cl.
    *A61B 5/00*      (2006.01)
(52) U.S. Cl.
    CPC .......... *A61B 5/7296* (2013.01); *A61B 5/0004* (2013.01); *A61B 5/0022* (2013.01);
    (Continued)

(58) Field of Classification Search
    CPC . A61B 5/0004; A61B 5/0022; A61B 5/14517; A61B 5/14546; A61B 5/1477;
    (Continued)

(56) References Cited

U.S. PATENT DOCUMENTS

| | | | |
|---|---|---|---|
| 2008/0146892 A1 | 6/2008 | LeBoeuf et al. | |
| 2016/0058376 A1 | 3/2016 | Baek et al. | |
| 2020/0008740 A1* | 1/2020 | Nishiyama | ............. A61B 5/486 |

FOREIGN PATENT DOCUMENTS

JP         2005-046305         2/2005

OTHER PUBLICATIONS

The Extended European Search Report dated Aug. 20, 2020 for the related European Patent Application No. 18828528.2.
(Continued)

*Primary Examiner* — Jonathan T Kuo
(74) *Attorney, Agent, or Firm* — Greenblum & Bernstein, P.L.C.

(57) ABSTRACT

A method includes: acquiring, via a network, biogas information at multiple timings and time information corresponding to time at each of the multiple timings, wherein the biogas represents a concentration of 2-ethylhexanoic acid of a user acquired by a sensor that detects the 2-ethylhexanoic acid discharged from a skin surface of the user; obtaining reference information representing a lower limit of a normal range of 2-ethylhexanoic acid per unit period of time, using a memory storing the reference information representing the lower limit of the normal range; determining a stress time period during which a concentration of the 2-ethylhexanoic acid of the user is less than the lower limit of the normal range, based on the acquired biogas information; and outputting time period information indicating the determined stress time period to an information terminal of the user.

10 Claims, 18 Drawing Sheets

(52) U.S. Cl.
CPC ............ *A61B 5/441* (2013.01); *A61B 5/4884* (2013.01); *A61B 5/6824* (2013.01)

(58) Field of Classification Search
CPC ....... A61B 5/165; A61B 5/441; A61B 5/4884; A61B 5/6801; A61B 5/6824; A61B 5/7296; G01N 2033/4975; G01N 27/622; G01N 33/497
See application file for complete search history.

(56) References Cited

OTHER PUBLICATIONS

Delgado-Povedano M M et al: "Development of a method for enhancing metabolomics coverage of human sweat by gas chromatography-mass spectrometry in high resolution mode", Analytica Chimica Acta, Elsevier, Amsterdam, NL, vol. 905, Dec. 17, 2015 (Dec. 17, 2015), pp. 115-125, XP029378631.

Dana Stingel et al: "Urinary 2-ethyl-3-oxohexanoic acid as major metabolite of orally administered 2-ethylhexanoic acid in human", Molecular Nutrition & Food Research, vol. 51, No. 3, Mar. 1, 2007 (Mar. 1, 2007), pp. 301-306, XP055721586.

Invitation pursuant to Rule 63(1) EPC dated Apr. 20, 2020 for the related European Patent Application No. 18828528.2.

S. Pennanen et al: "Distribution of 2-Ethylhexanoic Acid in Mice and Rats after an Intraperitoneal Injection", Pharmacology and Toxicology,vol. 68, No. 1, Jan. 1, 1991 (Jan. 1, 1991), pp. 57-59, XP055684014.

International Search Report of PCT application No. PCT/JP2018/021456 dated Sep. 4, 2018.

Japanese Cabinet Office, "White Paper on National Life (2008)", Chapter 1, Section 3, "2. Stressful Society and Modern pathology", Dec. 26, 2008 (Whole Sentence Translation).

General Conference (2013), Special Lectures, "Grasping Metal Problems of Pregnant Woman and Child Care", Keiko Yoshida, Child Health in Okinawa, vol. 41 (2014), Mar. 2014, pp. 3-8 (Whole Sentence Translation).

English Translation of Chinese Search Report dated Apr. 30, 2021 for the related Chinese Patent Application No. 201880011567.5.

\* cited by examiner

FIG. 4

| | DURING STRESS TASK | DURING RELAXATION TASK |
|---|---|---|
| No. 1 | 1.03 | 1 |
| No. 2 | 0.79 | 1 |
| No. 3 | 0.96 | 1 |
| No. 4 | 0.97 | 1 |
| No. 5 | 0.56 | 1 |
| No. 6 | 0.49 | 1 |
| No. 7 | 0.21 | 1 |
| No. 8 | 0.47 | 1 |
| No. 9 | 0.86 | 1 |
| No. 10 | 1.78 | 1 |
| No. 11 | 0.92 | 1 |
| No. 12 | 0.80 | 1 |
| No. 13 | 0.61 | 1 |
| No. 14 | 0.58 | 1 |
| No. 15 | 1.13 | 1 |
| No. 16 | 0.83 | 1 |
| No. 17 | 0.56 | 1 |
| No. 18 | 0.40 | 1 |
| No. 19 | 0.95 | 1 |
| No. 20 | 0.92 | 1 |
| AVERAGE | 0.79 | 1 |

INFORMATION PROVIDING METHOD, INFORMATION PROCESSING SYSTEM, INFORMATION TERMINAL, AND INFORMATION PROCESSING METHOD

TECHNICAL FIELD

The present disclosure relates to an information providing method and the like.

BACKGROUND ART

PTL 1 discloses a wristwatch-type conversation auxiliary device provided with a sweating sensor, a pulse sensor, and a blood flow sensor.

This wristwatch-type conversation auxiliary device measures feelings of a user wearing the wristwatch-type conversation auxiliary device with the sweating sensor, the pulse sensor, and the blood flow sensor, and displays results, acquired by applying information processing to the measurement results, with a character and the like. For example, the wristwatch-type conversation auxiliary device displays "feeling of anger" when measurement with the sweating sensor, the pulse sensor, and the blood flow sensor results in showing that a user has a feeling of anger. In addition, when the user has the feeling of anger, a message, "calm conversation is required", is displayed, for example.

PTL 1 also discloses a system allowing a wristwatch-type acquisition display device to display measurement results of a sweating sensor and a blood flow sensor, both of which are mounted inside a shoe, with a character and the like. Similarly to the above, when measurement with the sweating sensor and the blood flow sensor results in showing that a user has a feeling of anger, the "feeling of anger" is displayed.

PTL 1 also discloses a wristwatch-type conversation auxiliary device provided with a blood sensor including one or more painless needles. Change in feeling of the user is measured by measuring a substance in blood collected from the user. Then, processing similar to the above is performed.

PTL 1 also discloses a glasses-type conversation auxiliary device in which a small-sized camera and an eye camera are embedded. The small-sized camera measures nictitation and facial expression. The eye camera measures eye movement and nictitation. The glasses-type conversation auxiliary device displays results of information processing based on the measurement of nictitation and facial expression with the small-sized camera, and the measurement of eye movement and nictitation with the eye camera, in a transmission display inside a lens of the glasses-type conversation auxiliary device with a character and the like.

CITATION LIST

Patent Literature

PTL 1: Japanese Patent Application Publication No. 2005-46305

SUMMARY OF THE INVENTION

Technical Problem

Unfortunately, the conventional art described above is required to be further improved.

Solution to Problem

An aspect of the invention according to the present disclosure is a method for providing information in an information processing system, the method comprising:

acquiring, via a network, biogas information at multiple timings and time information corresponding to each of the multiple timings, wherein the biogas information represents a concentration of 2-ethylhexanoic acid of a user acquired by a sensor that detects the 2-ethylhexanoic acid discharged from a skin surface of the user;

obtaining reference information representing a lower limit of a normal range of the concentration of 2-ethylhexanoic acid per unit period of time, using a memory storing the reference information representing the lower limit of the normal range;

determining a stress time period during which a concentration of the 2-ethylhexanoic acid of the user is less than the lower limit of the normal range, based on the acquired biogas information; and outputting time period information indicating the determined stress time period to an information terminal of the user, to display the stress time period indicated by the time period information on a display of the information terminal.

Advantageous Effect of Invention

According to the above aspect, further improvement can be achieved.

BRIEF DESCRIPTION OF DRAWINGS

FIG. 4 is a list showing relative values of peak areas of 2-ethylhexanoic acid in mass spectrum data acquired when biogas collected from a hand of each of test subjects during the stress task is analyzed with a gas chromatography-mass spectrometry (GC/MS) by assigning 1 to a peak area of 2-ethylhexanoic acid in mass spectrum data acquired when biogas collected from the hand of each of the test subjects during the relaxation task is analyzed by the GC/MS.

DESCRIPTION OF EMBODIMENTS

Figure 1:
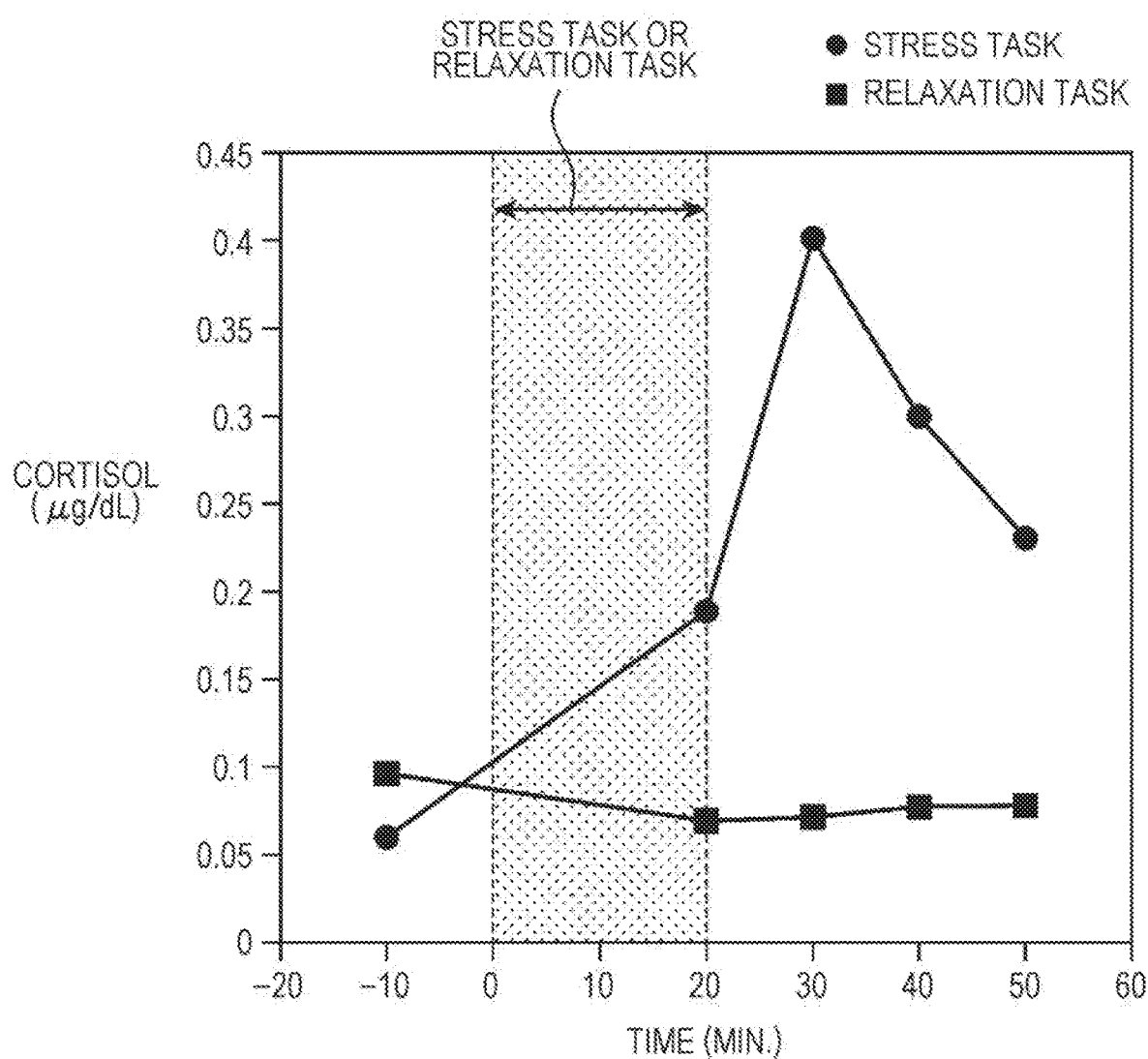
FIG. 1 is a graph showing temporal change in concentration of cortisol in saliva of a test subject before and after a stress task, and before and after a relaxation task.

Reason for Inventing an Aspect According to the Present Disclosure

First, a viewpoint of an aspect according to the present disclosure will be described.

The present inventors have researched a technique for objectively grasping invisible stress.

That is, while treatment of a mental disorder such as a depression is entrusted to a psychiatrist when it appears, the present inventors have researched prevention of a mental disorder such as a depression by grasping a sign of a mental disorder such as a depression before it appears.

The present inventors set a hypothesis that there is a kind of cause and effect relationship between stress and depression. That is, stress is not necessarily harmful for mind and body. However, accumulation of stress tends to have adverse effects on mind and body, so that it is conceivable that the adverse effects include depression.

Depression is classified into three causes such as (1) "physical", (2) "endogenous", and (3) "psychogenesis". The "physical" depression is caused by a characteristic of a brain or a bodily organ, or a medication. The "endogenous" depression is caused by a variation at a gene level, or by a factor causing mental disorder, naturally being included in a brain. The "psychogenesis" depression is caused by experience of psychological stress. It is difficult to strictly classify depression into these three kinds, and it is also said that the three kinds of depression is likely to appear while interacting with each other (refer to Japanese Cabinet Office "White Paper on National Life (2008)", Chapter 1, Section 3, "2. Stressful Society and Modern pathology, "http://www5.cao.go.jp/seikatsu/whitepaper/h20/10_pdf/01_honpen/pdf/08sh_0103_03. pdf). It can be said that a pregnant woman is under an environment allowing all the above kinds (1) to (3) of cause to be likely to be filled. During a gestation period, a pregnant woman cannot take a medicine and has restrictions on exercise, so that stress is less likely to be resolved. This may cause a pregnant woman to have a mental disorder such as a depression.

There is also a report that a postpartum depression is likely to appear within two weeks after giving birth (refer to General Conference (2013), Special Lectures," Grasping Metal Problem of Pregnant Woman and Child Care", Keiko Yoshida, Child Health in Okinawa, vol. 41 (2014) p. 3-8, http://www.osh.or.jp/in_oki/pdf/41gou/kouen.pdf). Thus, it is important to grasp a sign of a postpartum depression during a gestation period to prevent a postpartum depression. Besides a pregnant woman, an ordinary person also may have a mental disorder such as a depression due to stress on work or the like.

In consideration of the above, the present inventors have researched prevention of a mental disorder such as a depression by developing a tool of objectively grasping a level of stress accumulated on a person before the mental disorder such as a depression appears.

Here, cortisol, which is generally well known in relationship with stress, will be mentioned. The cortisol is a hormone that increases in secretion volume when a person is subjected to excessive stress. Thus, an inspection of a concentration of the cortisol enables an amount of stress at the time of the inspection to be grasped. The concentration of the cortisol can be measured by collecting saliva or blood, or by urine analysis. For example, a cumulative secretion volume of cortisol per day can be measured by collecting urine for 24 hours, so that an amount of stress per day also can be evaluated.

When the cortisol has a high concentration, Cushing's syndrome, stress, depression, anorexia nervosa, and the like are suspected. Meanwhile, when the cortisol has a low concentration, Addison's disease, congenital adrenal hyperplasia, ACTH psychosis, pituitary adrenocortical insufficiency, and the like are suspected.

As described above, while a concentration of cortisol is effective to evaluate stress, it is difficult to grasp temporal change in concentration of the cortisol due to unreality of continuous collection of saliva or blood, or continuous urine analysis that is unrealistic. Thus, it is also difficult to grasp temporal change in stress on a test subject.

Then, the present inventors set a hypothesis that biogas discharged from a skin surface of a person exists as an evaluation index of stress instead of the cortisol when mind and body are subjected to stress. To verify the hypothesis with an experiment, the present inventors performed experiments to specify biogas that has a correlation with stress.

Specifically, the present inventors allow each of thirty test subjects to perform a task for causing them to feel stress, and during a predetermined period of time before and after performing the task, saliva was collected from each of the test subjects and biogas was collected from an armpit and a hand of each of the test subjects at a predetermined time interval. Then, the present inventors made temporal change in concentration of cortisol acquired from the saliva collected as described above into a graph, and identified a test subject showing prominent temporal change in concentration of cortisol concentration. It was recognized that the test subject identified here felt stress with the task above.

Next, the present inventors analyzed 300 kinds of biogas collected from a hand of the test subject having felt stress in the above experiment to select a plurality of kinds of biogas being likely to have a correlation with stress. It was found that when stress was felt, 2-ethylhexanoic acid was less likely to be discharged from skin, by measuring the amount of the biogas discharged during performing the task and after performing the task in the biogas selected here. Hereinafter, a procedure in which 2-ethylhexanoic acid is determined to be less likely to be discharged from the skin of the test subject when the test subject feels stress will be described.

The present inventors built a psychology laboratory. The psychology laboratory is provided its inside with an isolated small room. The inside of the isolated small room can be seen from the outside thereof only through a glass window. The isolated small room is designed to apply psychological pressure to a test subject when a stress task is performed.

The present inventors guided thirty Japanese women in their twenties to forties serving as test subjects one by one into the psychology laboratory. Then, saliva of each of the test subjects was collected in the psychology laboratory. In ten minutes after saliva was collected from a test subject, the test subject grappled stress tasks such as a calculation problem, a speech; and the like for twenty minutes. For thirty minutes immediately after finish of the stress tasks, saliva was collected from the test subject once every ten minutes, i.e., four times in total. For the saliva collected here; a concentration of cortisol in each saliva was measured using a saliva cortisol quantitative kit (Salimetrics, LLC).

In parallel with the collection of saliva, biogas was collected from two places, a hand and an armpit, of the test subject for twenty minutes during the stress tasks and for twenty minutes from ten minutes to thirty minutes after the finish of the stress tasks. The biogas was collected from the hand by laying a gas-sampling bag on the hand of the test subject while fixing a wrist of the test subject with a rubber band, the inside of the gas sample bag being provided with an absorbent body for absorbing the biogas. The biogas was collected from the armpit by allowing the test subject to hold absorbent in the armpit. The absorbent held in the armpit was enclosed with cotton, and was fixed with a packing bag to prevent a position of the absorbent from being displaced in the armpit. The biogas was collected from the hand and the armpit as described above because sweat glands are concentrated in the hand and the armpit. Besides the hand and the armpit described above, the biogas may be collected from any portion in a skin surface.

In a day different from the day when the stress tasks were performed, the relaxation task was performed in place of the stress tasks. The relaxation task was performed according to procedures similar to those in the day when the stress tasks were performed to collect saliva and biogas from the test subjects. The relaxation task here was a work that caused the test subjects each to watch a DVD of natural scenery.

FIG. 1 is a graph showing temporal change in concentration of cortisol in saliva of a test subject before and after the stress task, and before and after the relaxation task. The vertical axis represents concentration (μg/dL) of cortisol, and the horizontal axis represents time (minute) from start of the stress task or the relaxation task. The concentration of cortisol increases upward in the vertical axis in FIG. 1, and as the concentration of cortisol increases, a test subject felt stress more as described above. The shaded portion in the graph of FIG. 1 (0 min. to 20 min, in the horizontal axis) is a period of time in which the stress task or the relaxation task was performed. As a publicly known fact, it is known that a concentration of cortisol in saliva increases in about 15 minutes after a test subject feels stress.

While in the graph of FIG. 1, the concentration of cortisol suddenly rises in 20 minutes after the start of the stress task (i.e., immediately after the finish of the stress task), there is little change found in the concentration of cortisol before and after the relaxation task. As a result, it is conceivable that the test subject showing the temporal change in the concentration of cortisol in FIG. 1 felt stress due to the stress task.

Meanwhile, there was a test subject who did not show temporal change in concentration of cortisol as described in FIG. 1. It is conceivable that this kind of test subject felt no stress due to the task to cause no cortisol in saliva to be secreted. Even when biogas of a test subject having felt no stress as described above is evaluated, a cause and effect relationship between stress and the biogas cannot be grasped. Thus, a test subject having felt no stress was eliminated from an evaluation object of the biogas. As described above, the top twenty test subjects (test subjects No. 1 to 20) having concentration of cortisol suddenly rising before and after the stress task among the thirty test subjects were identified.

Figure 2:
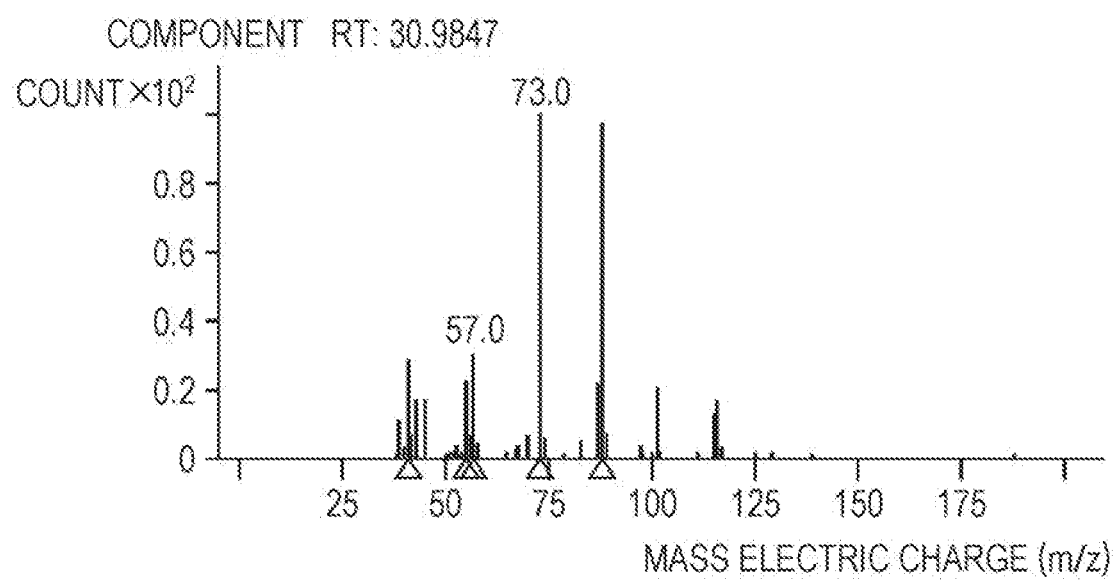
FIG. 2 shows mass spectrum data on 2-ethylhexanoic acid collected from a hand of a certain test subject.
Figure 3:
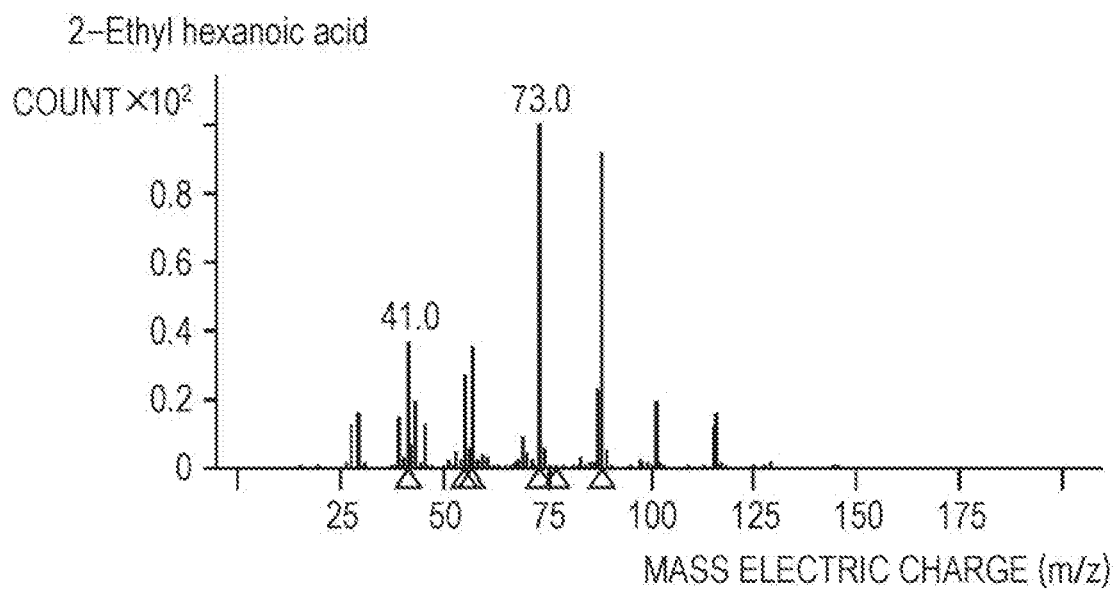
FIG. 3 shows mass spectrum data on 2-ethylhexanoic acid in the national institute of standards and technology (NIST) database.

Each of the absorbents collected (during the stress task and during the relaxation task) from a hand of each of the test subjects identified above was heated to desorb biogas of each of the test subjects, which had been absorbed in the corresponding one of the absorbents. Then, the desorbed biogas was analyzed with a gas chromatography-mass spectrometry (GC/MS (made of Agilent Technologies, Inc.)) to acquire mass spectrum data on the biogas. The mass spectrum data was compared with the national institute of standards and technology (NIST) database using analysis software of Agilent Technologies, Inc. to identify 2-ethylhexanoic acid. FIG. 2 shows mass spectrum data on 2-ethylhexanoic acid collected from the hand of the test subject, and FIG. 3 shows mass spectrum data on 2-ethylhexanoic acid in the NIST database. In comparison between the mass spectra in FIGS. 2 and 3, a similar spectrum peak is observed at an almost identical mass electric charge (m/z). As described above, it was identified that 2-ethylhexanoic acid was contained in the biogas.

Next, the present inventors calculated a peak area of a mass spectrum of each biogas discharged from a hand of each of the test subjects identified above (test subjects No. 1 to 20) during and after the stress tasks, as well as during and after the relaxation task, for each of the twenty test subjects above, and compared the peak area of each biogas during and after the stress tasks with that during and after the relaxation task to select a plurality of substances as candidates associated with stress from among components of the biogas, more than 300 kinds. Among the candidate substances, it was clearly found that 2-ethylhexanoic acid had a correlation with stress. The 2-ethylhexanoic acid has a chemical formula as follows.

CHEMICAL FORMULA 1

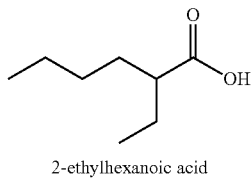

2-ethylhexanoic acid

Figure 5:
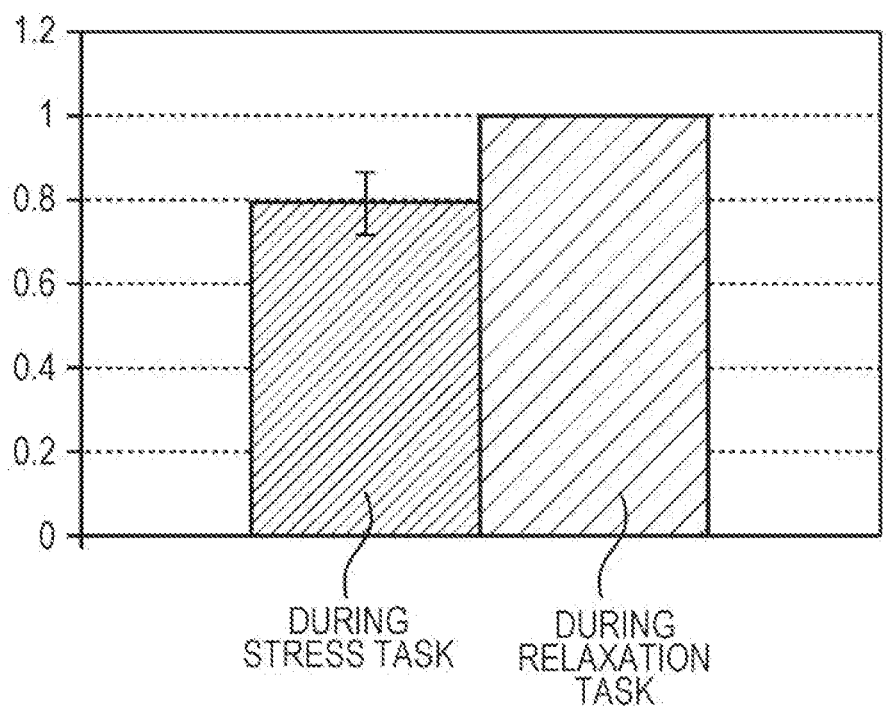
FIG. 5 is a bar graph showing an average value of relative values of respective peak areas and a deviation range, in the list of FIG. 4.

Next, a peak area of the 2-ethylhexanoic acid was calculated from the mass spectrum acquired with the GC/MS in each condition described above. A table shown in FIG. 4 is a list showing a ratio of peak areas of 2-ethylhexanoic acid in mass spectrum data acquired when biogas collected from the hand of each of test subjects during the stress task is analyzed with the GC/MS by assigning 1 to a peak area of 2-ethylhexanoic acid in mass spectrum data acquired when biogas collected from the hand of each of the test subjects during the relaxation task is analyzed with the GC/MS. FIG. 5 is a bar graph showing an average value of relative values of respective peak areas and a deviation range, in the list of FIG. 4. As shown in FIGS. 4 and 5, when a peak area of the 2-ethylhexanoic acid corrected during the relaxation task is assigned as 1, a ratio of a peak area of the 2-ethylhexanoic acid corrected during the stress tasks is less than 1.

From the results above, it was revealed that 2-ethylhexanoic acid was less likely to be discharged from the hand of the test subjects during the stress tasks as compared with that during the relaxation task. As a result, it can be said that the amount of discharge of 2-ethylhexanoic acid has a correlation with stress on the test subjects. Thus, 2-ethylhexanoic acid can serve as an index to objective evaluation of the amount of stress on a test subject. According to recognition of the present inventors, there is no example such as document about research associating the selected 2-ethylhexanoic acid with stress prior to the filing of the present application.

Based on the experiment results, The present inventors have identified 2-ethylhexanoic acid as biogas derived from stress. The present inventors believe that these findings have not found prior to the filing of the present application.

Next, a device for detecting 2-ethylhexanoic acid has been developed to succeed in objectively capturing stress that has been felt subjectively. That is, a method for measuring 2-ethylhexanoic acid discharged from a skin surface of a person with a device such as a sensor enables continuous measurement. In this case, it can be grasped when a stress reaction occurs in a day, what the person does when the stress reaction occurs, and the like. This enables temporal change in stress to be objectively grasped, so that it is expected that the stress can be controlled.

In addition, the present inventors have to lead the fact that measuring biogas derived from stress enables stress to be objectively grasped to a final purpose of preventing a mental disorder such as a depression. Each aspect of the invention according to the present disclosure relates to the above.

Based on the new findings acquired by the earnest research performed by The present inventors as described above, The present inventors have conceived each aspect according to the invention.

An aspect of the invention according to the present disclosure is a method for providing information in an information processing system, the method comprising:

acquiring, via a network, biogas information at multiple timings and time information corresponding to each of the multiple timings, wherein the biogas information represents a concentration of 2-ethylhexanoic acid of a user acquired by a sensor that detects the 2-ethylhexanoic acid discharged from a skin surface of the user;

obtaining reference information representing a lower limit of a normal range of the concentration of 2-ethylhexanoic acid per unit period of time, using a memory storing the reference information representing the lower limit of the normal range;

determining a stress time period during which a concentration of the 2-ethylhexanoic acid of the user is less than the lower limit of the normal range, based on the acquired biogas information; and outputting time period information indicating the determined stress time period to an information terminal of the user, to display the stress time period indicated by the time period information on a display of the information terminal.

In PTL 1, information on sweating, pulse, blood flow, nictitation, facial expression, and the like is used. Unfortunately, values indicated by these kinds of information vary when a person goes up and down stairs. Thus, these kinds of information have no relation to stress, and vary with a factor having no relation to stress. This causes the information not to be necessarily sufficient as a basis for objectively determining the amount of stress, and thus may cause a wrong determination.

In contrast, in the present aspect, the amount of stress is objectively determined using 2-ethylhexanoic acid that is biogas estimated to have a relationship with stress. This enables a cumulative level of stress to be objectively grasped without being affected by subjective feeling of a person.

As a result, a time period in which a concentration of 2-ethylhexanoic acid of the user is less than the lower limit of the normal range is determined based on the biogas information, and information indicating the time period determined is output to the information terminal of the user. This enables a state of stress on the person to be objectively recognized by the person, so that it can be expected that a depression such as a mental disorder is prevented.

In addition, a user does not grasp what is a stressor (stress factor) for the user in many cases. When the information terminal displays a time period in which a concentration of 2-ethylhexanoic acid of the user is less than the lower limit of the normal range, the user can objectively grasp how much the amount of stress was felt in a day by recalling the day, for example. In addition, the present aspect enables a stressor of the user to be found out with a clue of an incident having occurred to the user in the time period in which the concentration of 2-ethylhexanoic acid of the user is less than the lower limit of the normal range.

As described above, it can be also grasped when a stress reaction occurs in a day, what the user does when the stress reaction occurs, and the like, for example. This enables stress to be objectively grasped, so that it is expected that the stress can be controlled.

In the present aspect, the lower limit of the normal range of the concentration of 2-ethylhexanoic acid per unit period of time may be set for the user as individual information of the user, based on the biogas information acquired in a predetermined period of time.

In this case, data on the user itself is used as a reference value. The amount of discharge of 2-ethylhexanoic acid is affected by age, food, weight, and the like to cause an individual difference, so that it is preferable to use data on the user itself for accurate determination.

In contrast, there is no disclosure about how to have reference information in PTL 1.

According to the present aspect, a level of stress is determined using data on the user itself as a reference value. This enables determination suitable for an individual.

In the present aspect, the lower limit of the normal range of the concentration of 2-ethylhexanoic acid per unit period of time may be used commonly to a plurality of users including the user.

In this case, the reference value is used common to the plurality of users to save time for generating and managing a reference value for each of the users.

In the present aspect, the stress time period indicated by the time period information may be displayed in association with schedule information on the user, on the information terminal In this case, the user checks the schedule information against a time period with high stress to enable a cause and effect relationship between stress and an action of the user itself to be easily checked.

In the present aspect, the sensor for detecting 2-ethylhexanoic acid may be built in a device to be worn on an arm of the user.

In this case, the sensor for detecting 2-ethylhexanoic acid is built in the device worn on an arm of the user, so that an object worn on the arm of the user in daily life may have a function of the sensor, for example. As a result, user's inconvenience of wearing a sensor can be reduced.

In the present aspect, the time information corresponding to each of the multiple timings may be associated with each time when the sensor detects the biogas.

In this case, whether a concentration of 2-ethylhexanoic acid is less than the lower limit of the normal range at the time is determined, when the sensor captures biogas, so that a time period with stress can be accurately notified to the user. In the present aspect, the text, "associated with each time when the biogas is captured", may indicate time when the sensor measures biogas information, or time when a processor such as a server acquires biogas information from the sensor via a network.

An information processing system according to another aspect of the present disclosure includes a server device and an information terminal, wherein the server device is configured to:

acquire, via a network, biogas information at multiple timings and time information corresponding to time at each of the multiple timings, wherein the biogas information represents a concentration of 2-ethylhexanoic acid of a user acquired by a sensor that detects the 2-ethylhexanoic acid discharged from a skin surface of the user obtain reference information representing a lower limit of a normal range of the concentration of 2-ethylhexanoic acid per unit period of time, using a memory storing the reference information representing the lower limit of the normal range;

determine a stress time period during which a concentration of the 2-ethylhexanoic acid of the user is less than the lower limit of the normal range, based on the acquired biogas information; and output time period information indicating the determined stress time period to the information terminal, and wherein the information terminal displays the stress time period indicated by the time period information, on a display of the information terminal.

An information terminal according to yet another aspect of the present disclosure may be used in the information processing system described above.

A method for processing information according to yet another aspect of the present disclosure uses a computer, and includes the steps of:

acquiring, via a network, biogas information at multiple timings and time information corresponding to time at each of the multiple timings, wherein the biogas information represents a concentration of 2-ethylhexanoic acid of a user acquired by a sensor that detects the 2-ethylhexanoic acid discharged from a skin surface of the user;

obtaining reference information representing a lower limit of a normal range of the concentration of 2-ethylhexanoic acid per unit period of time, using a memory storing the reference information representing the lower limit of the normal range;

determining a stress time period during which a concentration of the 2-ethylhexanoic acid of the user is less than the lower limit of the normal range, based on the acquired biogas information; and outputting notice information representing that stress on the user is less than a lower limit of a predetermined normal range within the determined stress time period to display the notice information on a display.

According to the present aspect, when a concentration of 2-ethylhexanoic acid is less than the lower limit of the normal range, the information showing that stress on the user is less than the normal range is displayed in the display. In contrast, when a concentration of 2-ethylhexanoic acid is equal to or more than the lower limit of the normal range, information showing that stress on the user is within the normal range is displayed in the display. This enables a result of objective determination whether the user is in a stress state at present to be notified to the user.

First Embodiment

Estimate Data

Figure 6A:
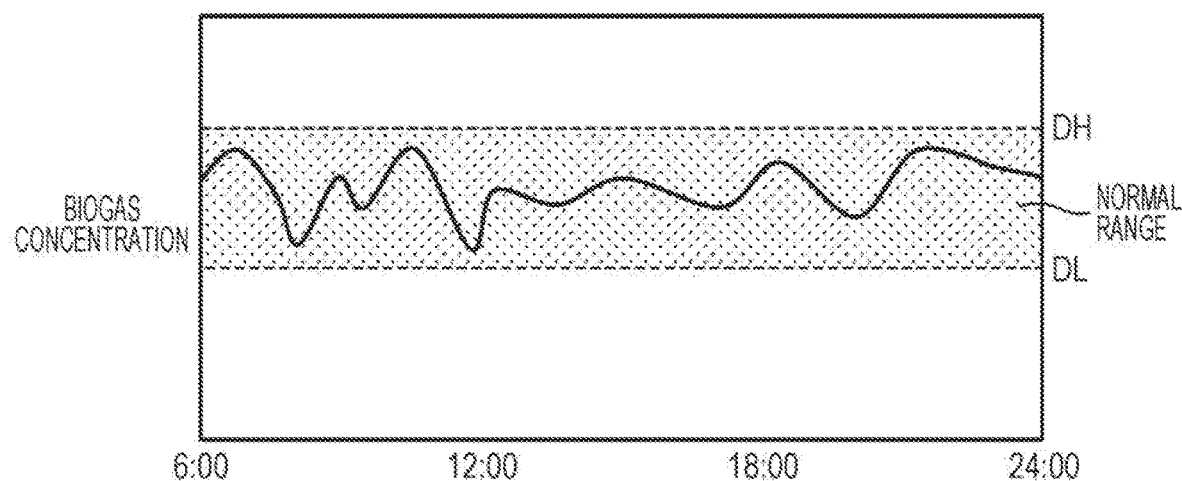
FIG. 6A is a graph showing estimated data on biological data used in a first embodiment of the present disclosure.
Figure 6B:
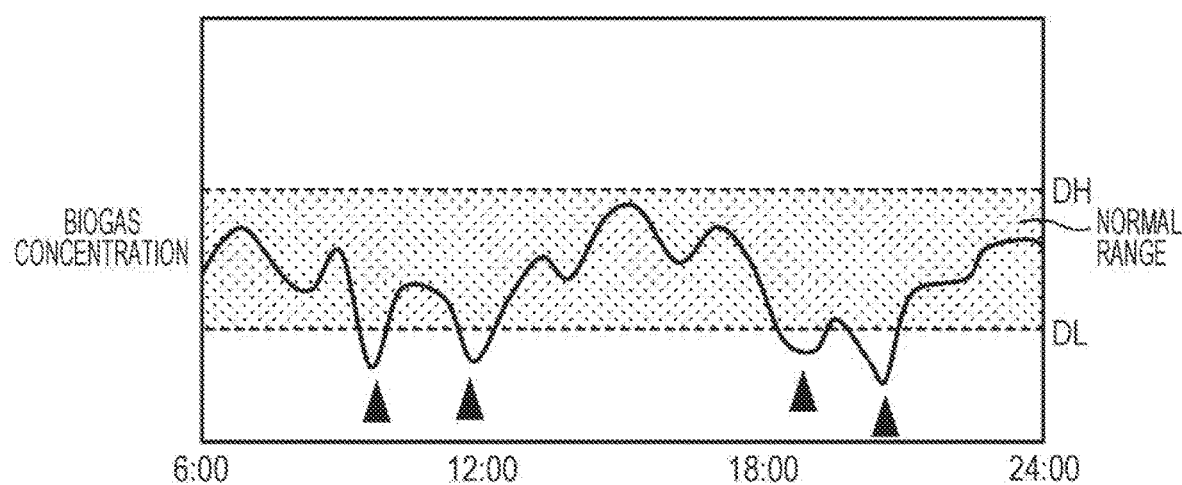
FIG. 6B is a graph showing estimated data on biological data used in the first embodiment of the present disclosure.

FIGS. 6A and 6B are each a graph showing estimated data on biological data used in the first embodiment of the present disclosure. In each of FIGS. 6A and 6B, the vertical axis represents biogas concentration (an example of biogas information), and the horizontal axis represents time. The estimated data does not show measurement values of biological data that are actually measured, and is only data acquired by estimating the biological data. The biological data is measured by a sensor worn by a user as described below. The biological data shows a measurement value of concentration of biogas to be measured (biogas concentration) among biogas discharged from a skin surface of a user. In the present disclosure, the biogas to be measured is 2-ethylhexanoic acid. The biogas concentration has a unit of $\mu g/dL$, for example.

FIG. 6A shows a temporal transition of biological data on a user without stress, and FIG. 6B shows a temporal transition of biological data on the user with stress. As shown in FIG. 6A, the biological data without stress has biogas concentration within a normal range. In contrast, as shown in FIG. 6B, the biological data with stress has biogas concentration that is frequently less than lower limit DL of the normal range. FIG. 6B shows an example in which the biogas concentration is less than lower limit DL four times in a time period from six o'clock to twenty-four o'clock.

In the present disclosure, a mental disorder such as a depression is prevented by determining a time period with biogas concentration less than lower limit DL and notifying information indicating the time period determined to a user.

Sensor

Figure 7:
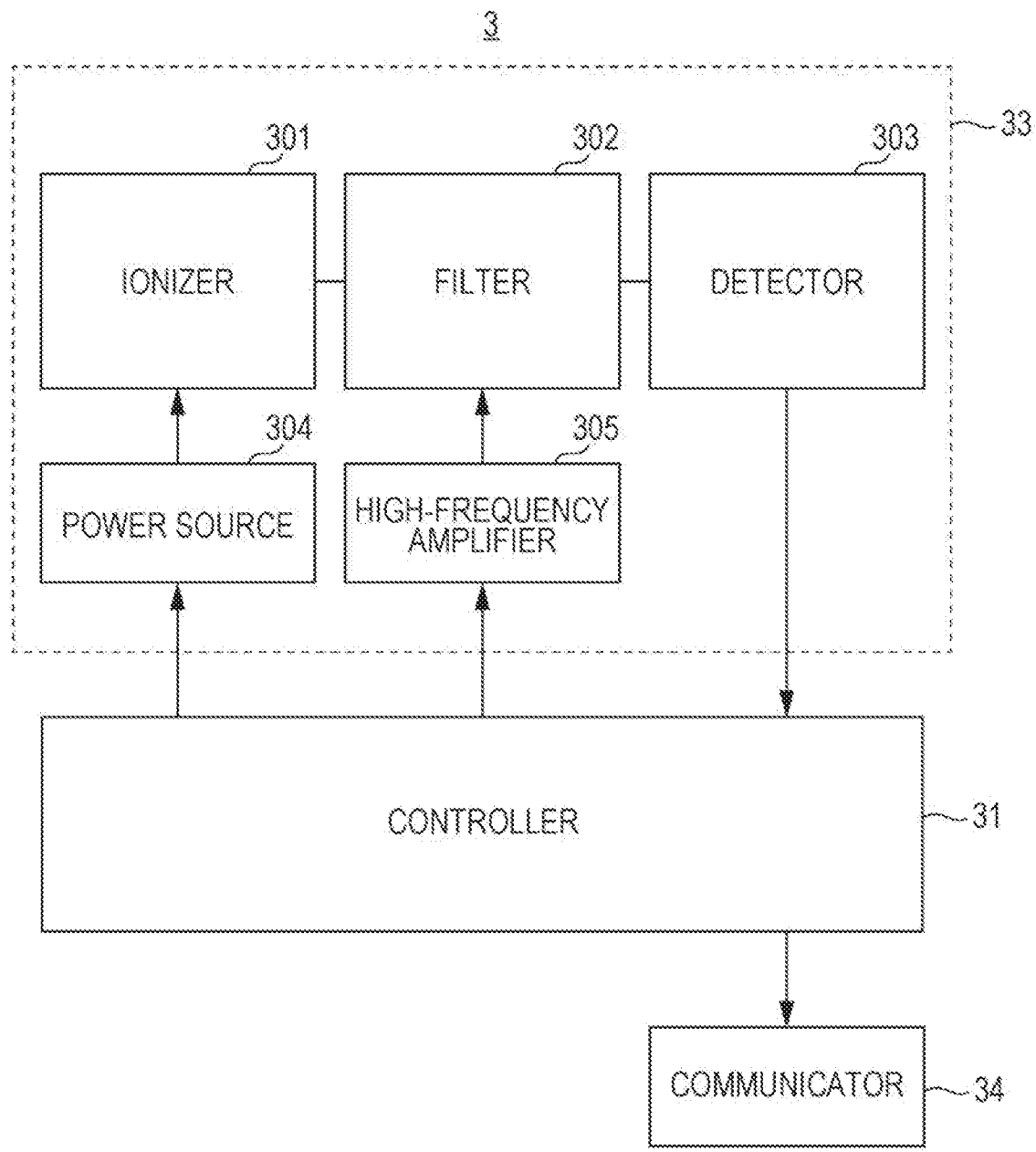
FIG. 7 is a block diagram illustrating an example of a configuration of a sensor that measures biological data in the first embodiment of the present disclosure.

FIG. 7 is a block diagram illustrating an example of a configuration of sensor 3 that measures biological data in the first embodiment of the present disclosure.

In the present disclosure, a sensor using a technique of field asymmetric ion mobility spectrometry (FAIMS) is used as the sensor 3, for example. The field asymmetric ion mobility spectrometry is used to selectively separate at least one kind of substance from a mixture containing two or more kinds of substance.

Sensor 3 comprises detector 33, controller 31, and communicator 34. Detector 33 comprises ionizer 301, filter 302, detector 303, power source 304, and high-frequency amplifier 305. In FIG. 7, arrows each indicate a flow of an electric signal, and lines connecting ionizer 301, filter 302, and detector 303 indicate a flow of biogas.

Power source 304 and high-frequency amplifier 305 are used to drive ionizer 301 and filter 302, respectively. Filter 302 separates only desired biogas (2-ethylhexanoic acid in the present disclosure) from among biogas ionized using ionizer 301, and detector 303 detects the amount of ions which have passed through filter 302 so that information indicating biogas concentration is acquired. The information acquired is output via communicator 34. Driving of sensor 3 is controlled by controller 31.

Figure 8:
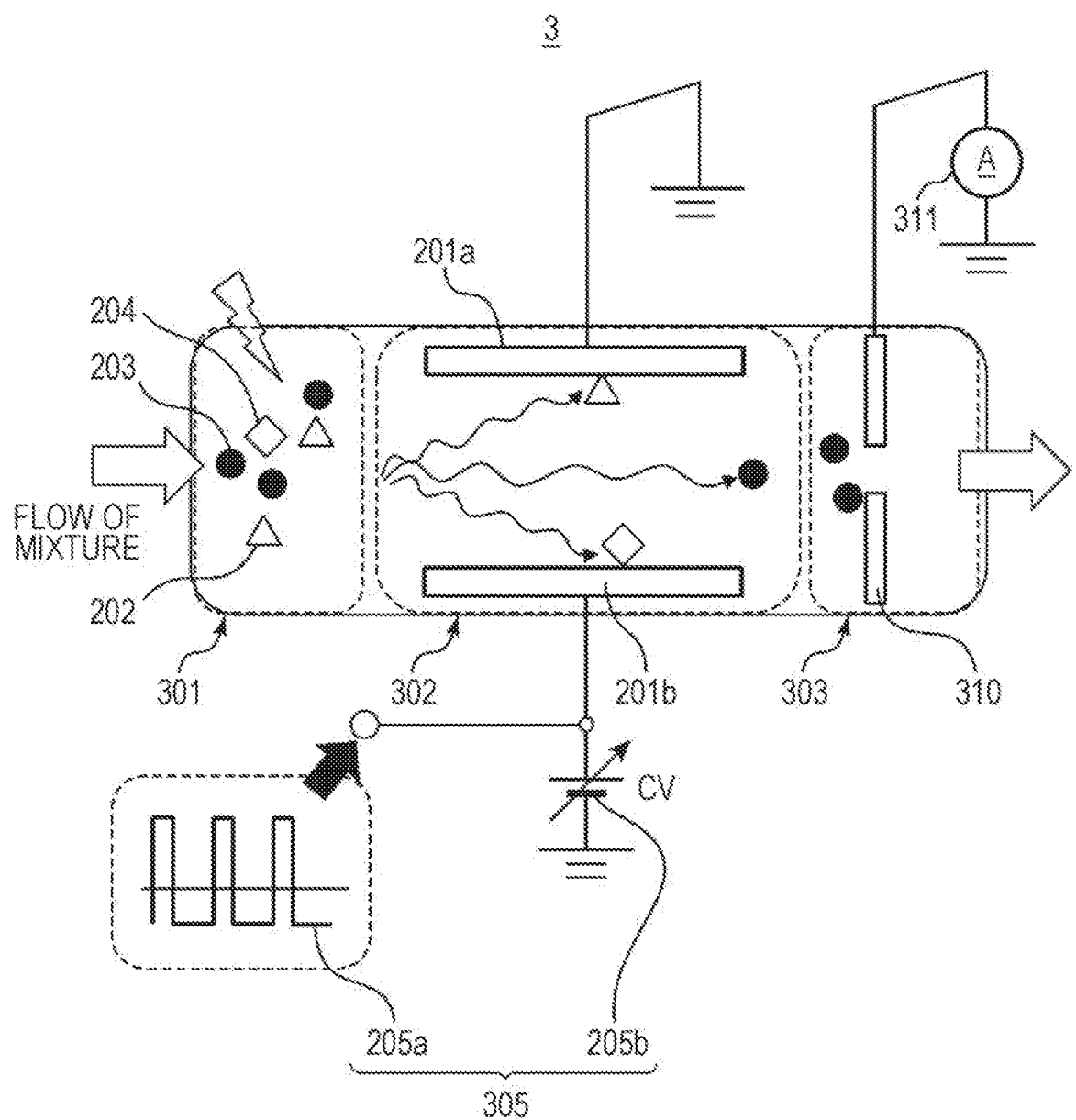
FIG. 8 illustrates operation of the sensor illustrated in FIG. 7 in more detail.

FIG. 8 illustrates operation of sensor 3 illustrated in FIG. 7 in more detail. A mixture supplied to ionizer 301 is biogas discharged from a skin surface of a user. Ionizer 301 may include an inlet for taking in biogas discharged from a skin surface of a user. The inlet may be provided with absorbent for absorbing biogas. The inlet may be further provided with a heater for separating biogas absorbed in the absorbent from the absorbent. FIG. 8 shows an example in which the mixture contains three kinds of gas 202 to 204, for convenience of explanation. Gas 202 to 204 is ionized using ionizer 301.

Ionizer 301 comprises a corona-discharging source, a radiation source, and the like to ionize gas 202 to 204. Gas 202 to 204 ionized is supplied to filter 302 disposed adjacent to ionizer 301. The corona-discharging source and the radiation source, constituting ionizer 301, are driven by voltage supplied from power source 304.

Filter 302 includes first electrode 201a in a planar shape and second electrode 201b in a planar shape, being disposed parallel to each other. First electrode 201a is grounded. Meanwhile, second electrode 201b is connected to high-frequency amplifier 305.

High-frequency amplifier 305 includes AC voltage source 205a that generates asymmetric AC voltage, and variable voltage source 205b that generates compensation voltage CV being DC voltage. AC voltage source 205a generates asymmetric AC voltage and applies it to second electrode 201b. Variable voltage source 205b is connected at one end to second electrode 201b, and at the other end to the ground. Then, the asymmetric AC voltage generated by AC voltage source 205a is superposed on compensation voltage CV, and is supplied to second electrode 201b.

Three kinds of gas 202 to 204 ionized are supplied to a space between first electrode 201a and second electrode 201b. Three kinds of gas 202 to 204 are affected by an electric field generated between first electrode 201a and second electrode 201b.

Figure 9:
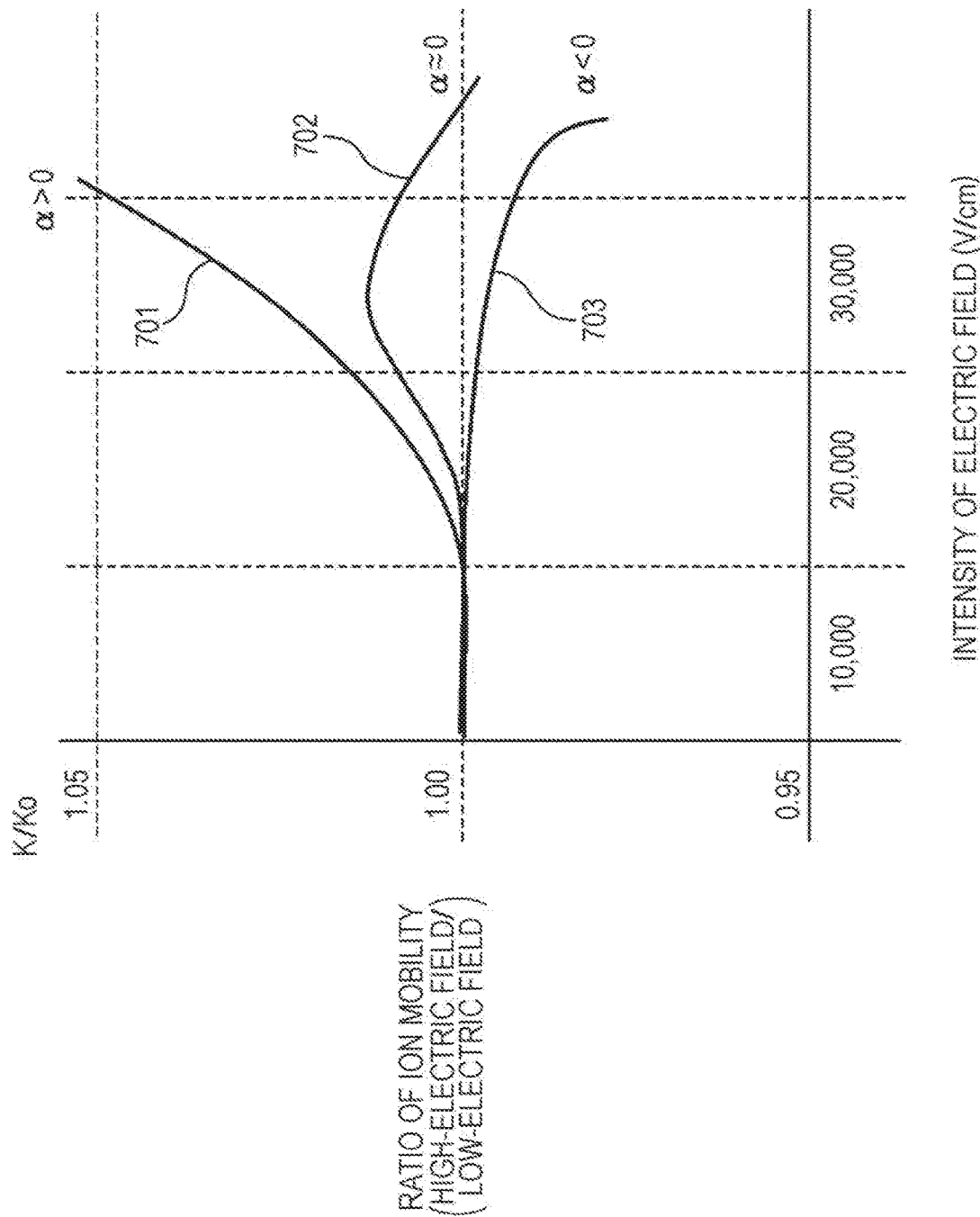
FIG. 9 is a graph showing a relationship between intensity of an electric field and a ratio of ion mobility.

FIG. 9 is a graph showing a relationship between intensity of an electric field and a ratio of ion mobility, its vertical axis representing the ratio of ion mobility, and its horizontal axis representing intensity (V/cm) of the electric field. α is a coefficient determined depending on a kind of ion. The ratio of ion mobility is a ratio of mobility in a high-electric field to mobility in a boundary of a low-electric field.

As indicated by curve 701, ionized gas with a coefficient α more than zero moves more actively as intensity of electric field increases. An ion with a mass-to-charge ratio less than 300 shows this kind of movement.

As indicated by curve 702, ionized gas with a coefficient α of almost zero moves more actively as intensity of electric field increases; however, the mobility decreases as the intensity of the electric field further increases.

As indicated by curve 703, ionized gas with a negative coefficient α decreases in mobility as intensity of electric field increases. An ion with a mass-to-charge ratio of 300 or more shows this kind of movement.

Due to difference in characteristics of mobility as described above, each of three kinds of gas 202 to 204 proceeds inside filter 302 in a different direction as illustrated in FIG. 8. FIG. 8 illustrates an example in which while only gas 203 is discharged through filter 302, gas 202 is trapped on a surface of first electrode 201a, and gas 204 is trapped on a surface of second electrode 201b. As a result, only gas 203 is selectively separated from three kinds of gas 202 to 204, and discharged through filter 302. That is, sensor 3 can discharge desired gas through filter 302 by appropriately setting intensity of the electric field. The intensity of the electric field is determined in accordance with a voltage value of compensation voltage CV and a waveform of asymmetric AC voltage generated by AC voltage source 205a. Thus, sensor 3 can discharge biogas to be measured through filter 302 by setting the voltage value of compensation voltage CV and the waveform of asymmetric AC voltage, respectively, to a voltage value and a waveform, predetermined in accordance with a kind of the biogas to be measured (2-ethylhexanoic acid in the present disclosure).

Detector 303 is disposed adjacent to filter 302. That is, filter 302 is disposed between ionizer 301 and detector 303. Detector 303 comprises electrode 310 and ammeter 311 to detect gas 203 which has passed through filter 302.

Gas 203 which has reached detector 303 transfers electric charge to electrode 310. A value of an electric current which flows in proportion to the amount of the transferred electric charge is measured with Ammeter 311. From the value of the electric current measured by ammeter 311, a concentration of gas 203 is measured.

Network Configuration

Figure 10:
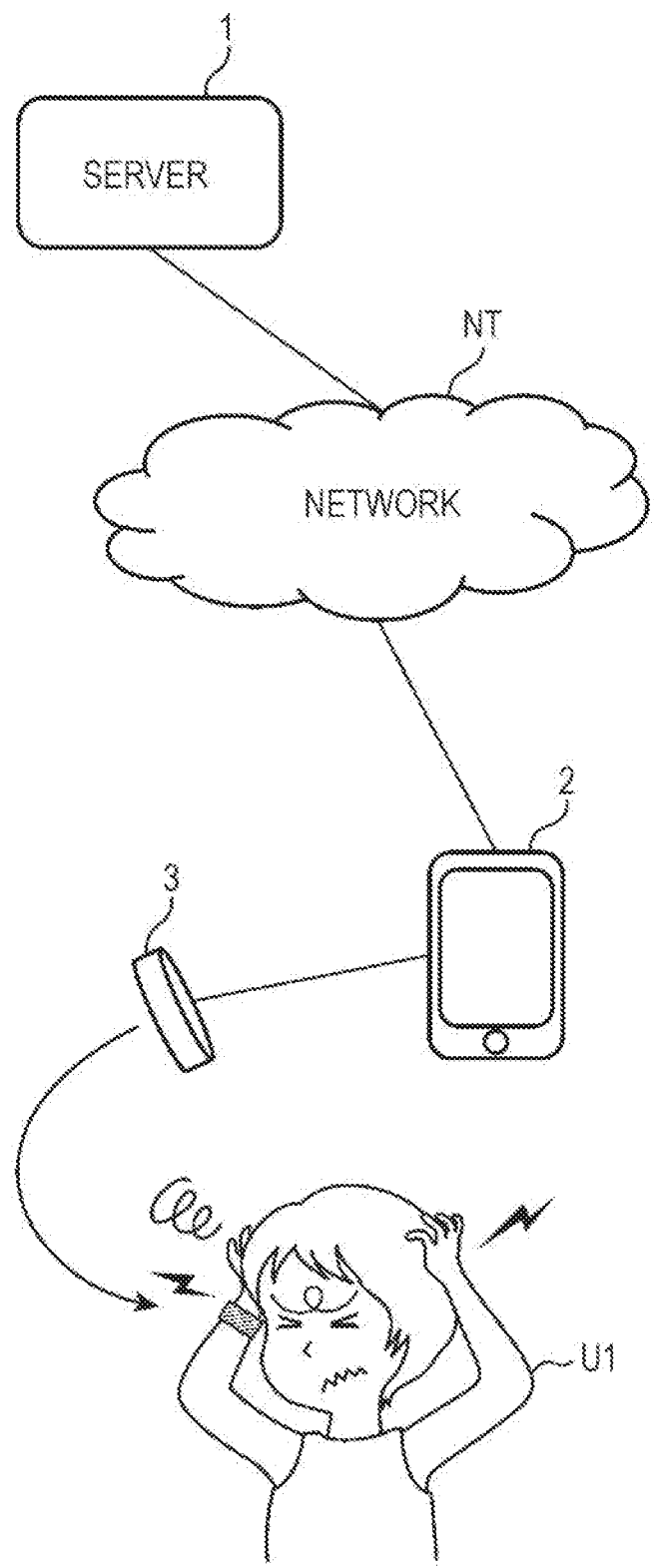
FIG. 10 illustrates an example of a network configuration of an information processing system according to the first embodiment of the present disclosure.

FIG. 10 illustrates an example of a network configuration of an information processing system according to the first embodiment of the present disclosure. The information processing system provides a care service for taking care of stress on user U1. The care service is provided, for example, by an insurance company or the like with which user U1 is contracted. Actual operation of the care service may be performed, for example, by a manufacturer that manufactures sensor 3 commissioned by the insurance company. The care service may be provided by a service provider different from an insurance company providing the care service.

The insurance company provides insurance service such as life insurance and medical insurance to user U1, for example. Then, the insurance company lends sensor 3 to user U1, for example, and acquires biological data of user U1 to manage a state of stress on user U1, thereby preventing illness due to a mental disorder of user U1. This allows the insurance company to save expenditure for insurance. The care service urges user U1 to wear sensor 3, so that user U1 may feel a burden. Then, the insurance company may provide an insurance plan for reducing an insurance fee borne by user U1 in exchange for the care service.

The information processing system comprises server 1 (an example of the server device), user terminal 2 (an example of the information terminal), and sensor 3.

Server 1 and user terminal 2 are communicatively connected to each other via network NT. Network NT is composed of the Internet communication network, a cellular phone communication network, and a network including a public telephone network. Sensor 3 and user terminal 2 are communicatively connected to each other via near field communication such as a wireless LAN of IEEE802.11b, or Bluetooth (registered trademark: IEEE802.15.1), for example.

Server 1 is composed of a cloud server including one or more computers, for example. Server 1 includes a processor such as a CPU or an FPGA, and a memory. Server 1 acquires biological data on user U1 measured with sensor 3 via user terminal 2 and network NT to determine whether biogas concentration is within the normal range.

User terminal 2 is composed of a portable information processor such as a smartphone, a tablet terminal, or the like, for example. The user terminal 2 may be composed of a desktop computer. User terminal 2 is possessed by user U1.

Sensor 3 is worn on an arm of user U1 for example, to detect a concentration of biogas discharged from a hand of user U1. Sensor 3 comprises a mounting belt, for example, and a user winds the mounting belt around its wrist (an example of an arm) to wear sensor 3 near the hand. This enables sensor 3 to detect biogas discharged from the hand. However, this is an example. For example, sensor 3 may be built in a wristwatch-type wearable terminal. The wristwatch-type wearable terminal is an example of a device to be worn by a user.

Figure 11:
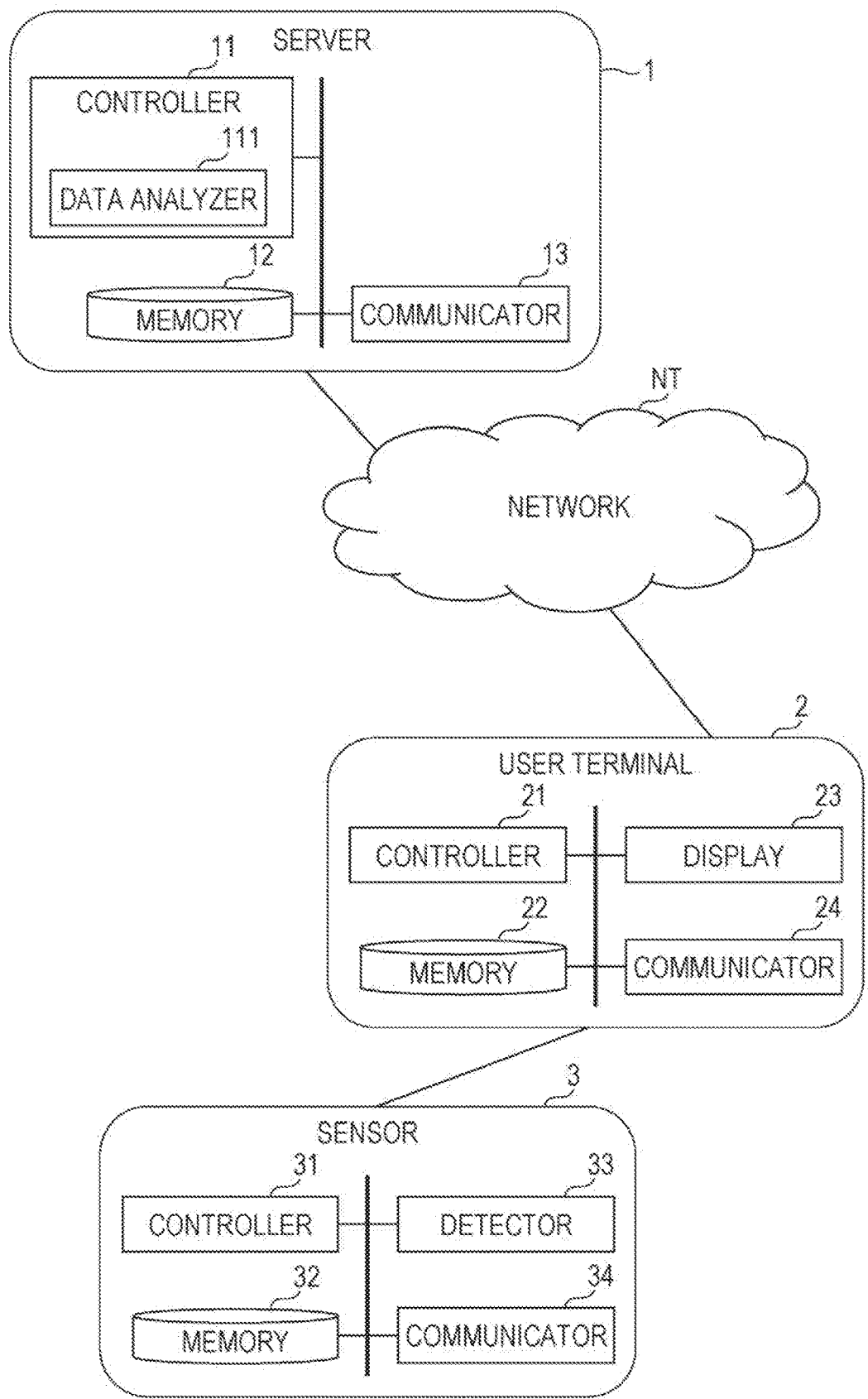
FIG. 11 is a block diagram illustrating an example of a detailed configuration of the information processing system illustrated in FIG. 10.

FIG. 11 is a block diagram illustrating an example of a detailed configuration of the information processing system illustrated in FIG. 10. Server 1 comprises controller 11, memory 12, and communicator 13. Controller 11 is composed of a processor, and comprises data analyzer 111. Data analyzer 111 serves when the processor executes a program for causing a computer to perform the information providing method of the present disclosure, stored in memory 12, for example. The program for causing a computer to perform the information providing method of the present disclosure may be provided by download through a network, or may be provided by being stored in a computer-readable nontemporary recording medium.

When communicator 13 receives biological data acquired by sensor 3, data analyzer 111 acquires the biological data from communicator 13. Then, data analyzer 111 reads out information indicating lower limit DL of the normal range of biogas concentration from memory 12, and determines a time period in which biogas concentration indicated by the biological data is less than lower limit DL. Data analyzer 111 then registers the biological data in biological data table T4 (FIG. 12) stored in memory 12 while associating it with the determination result. In addition, when biological data for a predetermined period of time (e.g., one day, half a day, two days, one week, and one month) is accumulated, data analyzer 111 transmits information indicating a time period in which biogas concentration is less than lower limit DL (referred to below as "time-period information") in the biological data for the predetermined period of time to user terminal 2 via communicator 13.

Figure 12:
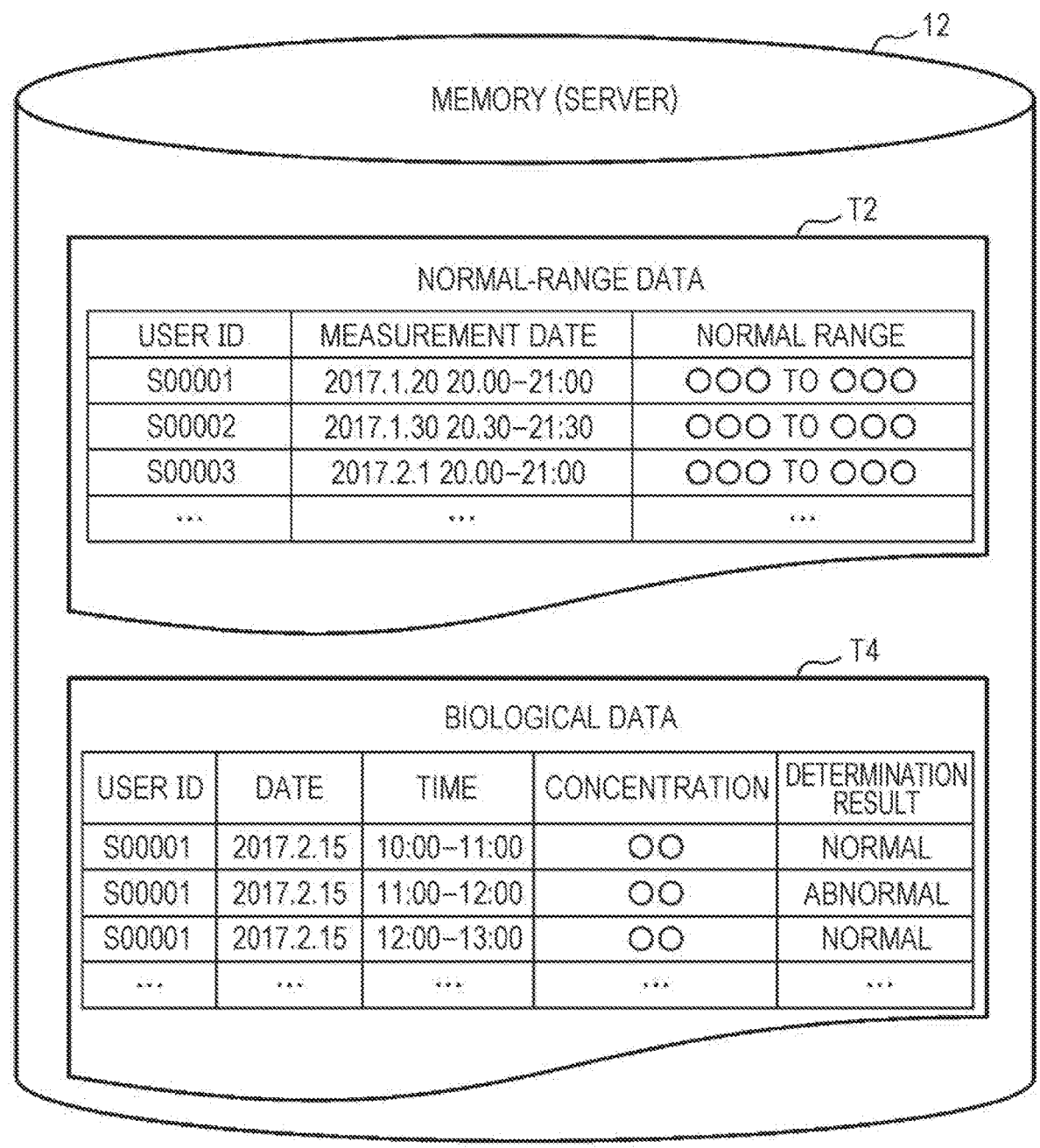
FIG. 12 illustrates an example of data organization of a table stored in a memory.

Memory 12 stores information indicating the normal range of biogas concentration. As illustrated in FIG. 12, memory 12 stores normal-range data table T2 and biological data table T4 in the present disclosure, FIG. 12 illustrates an example of data organization of a table stored in memory 12.

Normal-range data table T2 stores a normal range of stress in biogas concentration of one or more users using care service. In normal range data table T2, one record is assigned to one user, and "user ID", "measurement date", and "normal range" are stored while being associated with each other.

A "user ID" field stores an identifier for uniquely identifying a user using care service. A "measurement date" field stores a time period in a measurement date of biological data used for calculating a normal range. A "normal range" field stores the normal range calculated by using biological data stored in the "measurement date" field. The "normal range" field also stores lower limit DL and upper limit DH of the normal range.

For example, with regard to a user with a user ID "S00001", the normal range thereof is calculated using biological data measured in a time period from twenty o'clock to twenty-one o'clock on Jan. 20, 2017.

As described above, a normal range for each of users is calculated in the present disclosure, so that stress on each of the users can be determined using a normal range suitable for the corresponding one of the users to enable increase in determination accuracy. While the normal range for each of the users is calculated in the present disclosure, this is an example, and thus an average value of normal ranges calculated in a part of all the users may be used as a normal range for all the users. Alternatively, an average value of normal ranges of all the users may be used as a normal range for all the users. In these cases, a normal range is not required to be stored and calculated for each of the users, so that the amount of memory consumption can be saved and processing steps can be reduced.

Biological data table T4 stores biological data acquired by sensor 3. In biological data table T4, one record is assigned to one biological data, and "user ID", "date", e, "concentration", and "determination result" are stored while being associated with each other.

A "user ID" field stores a user ID identical to the user ID stored in normal-range data table T2. A "date" field stores a measurement date of biological data. A "time" field stores a time period in which the biological data is measured. A "concentration" field stores biogas concentration indicated by the biological data. A "determination result" field stores a result of determination whether the biogas concentration is within the normal range. The "time" field may store a time period in which server 1 acquires the biological data.

For example, in the record on the first line in the biological data table 4, biological data on biogas concentration "00" of a user with a user ID "300001", measured in a time period from ten o'clock to eleven o'clock on Feb. 15, 2017 is stored. In the first record, since the biogas concentration is within the normal range, "normal" is stored in the "determination result" field, because. Meanwhile, in the second record, since the biogas concentration out of the normal range, "abnormal" is stored in the "determination result" field.

While biological data table T4 shows only the biological data on the user with the user ID "S00001", this is only an example, and biological data table T4 stores biological data on all users using the care service.

FIG. 11 is referred again. Communicator 13 is composed of a communication circuit connecting server 1 to network NT, for example, and not only receives biological data measured with sensor 3, but also transmits time-period information to user terminal 2.

User terminal 2 comprises controller 21, memory 22, display 23 (an example of the display), and communicator 24. Controller 21 is composed of a processor such as a CPU, and controls the whole of user terminal 2. The memory 22 stores various data. In the present disclosure, memory 22 particularly stores an application to be executed in user terminal 2 to cause user U1 to use the care service. Memory 22 also stores a user ID transmitted in association with biological data.

Display 23 is composed of a display comprising a touch panel, for example, and displays various kinds of information. In the present disclosure, display 23 particularly displays the time-period information. Communicator 24 connects user terminal 2 to network NT, and is composed of a communication circuit for allowing user terminal 2 to communicate with sensor 3. In the present disclosure, communicator 24 particularly receives biological data transmitted from sensor 3, and transmits the received biological data to server 1 while associating it with a user ID stored in memory 22. In the present disclosure, communicator 24 particularly receives the time-period information transmitted from server. Display 23 does not have to be composed of a touch panel. In this case, user terminal 2 may comprise an operation section that receives operation from a user.

Sensor 3 comprises controller 31, memory 32, detector 33, and communicator 34. Controller 31 is composed of a processor such as a CPU, a DSP, or the like and controls the whole of sensor 3. Memory 32 temporarily stores biological data measured by detector 33, for example. Memory 32 also stores data (e.g., frequency, positive amplitude, and negative amplitude) required for AC voltage source 205a to generate asymmetric AC voltage. Memory 32 also stores a voltage value of compensation voltage CV.

Communicator 34 is composed of a communication circuit such as a wireless LAN or Bluetooth (registered trademark), and transmits biological data measured by detector 33 to user terminal 2. The biological data is received by communicator 24 of user terminal 2, and transmitted to server 1 via network NT.

Sequence

Figure 13:
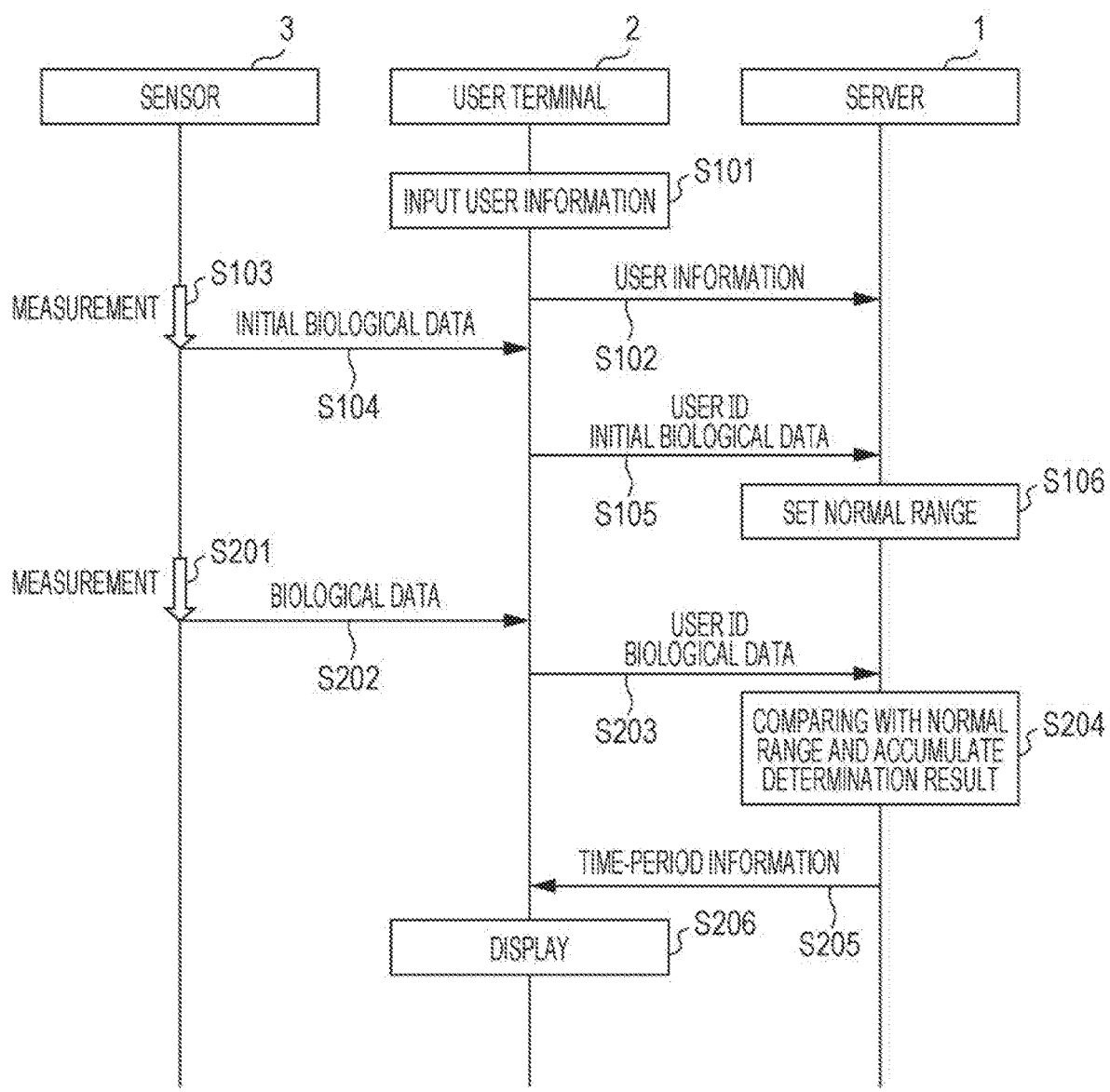
FIG. 13 is a sequence diagram illustrating an example of processing of a biological information system illustrated in FIG. 11.

FIG. 13 is a sequence diagram illustrating an example of processing of a biological information system illustrated in FIG. 11. The sequence diagram is divided into initial phases from S101 to S106 and normal phases after S201. The initial phases are performed to calculate a normal range of a user, and performed immediately after introduction of care service. The normal phases are preformed to monitor a state of stress on the user using the normal range calculated in the initial phases.

The initial phases are performed when a user first starts an application for user terminal 2 to use care service in user terminal 2, for example.

First, display 23 of user terminal 2 receives input of user information (S101). Display 23 here may display a registration screen for causing the user to input the user information such as a user ID, a telephone number, an e-mail address, an SNS account and the like into the registration screen. As the user ID, a user ID issued when the user made an insurance contract with the insurance company may be used, for example. Alternatively, as the user ID, a user ID issued when server 1 receives the user information in S102 described below may be notified to user terminal 2. In this case, the user is not required to input the user ID into the registration screen.

Next, controller 21 of user terminal 2 causes communicator 24 to transmit the received user information to server 1 (S102). The transmitted user information is stored in a user information table (not illustrated) for managing user information on one or more users using the care service by controller 41 of server 1.

Subsequently, detector 33 of sensor 3 measures initial biological data on the user (3103). Next, controller 31 of sensor 3 causes communicator 34 to transmit the measured initial biological data to user terminal 2 (S104).

When communicator 24 receives the initial biological data in user terminal 2, controller 21 transmits the initial biological data to server 1 while associating the initial biological data with the user ID (S105).

The initial biological data is used for calculating a normal range of the user based on the premise that the user is not in a stress state. Then, when the transmission of the user information is finished (S102), user terminal 2 may display a message such as "to measure biological data, wear the sensor and stay quiet for a while", for example, in display 23. Data analyzer 111 of server 1 sets the normal range (S106). The normal range set is stored in normal-range data table T2 by data analyzer 111 of server 1 while being associated with the user ID.

Up to this point, the initial phases are finished. After this, the normal phases are performed.

First, detector 33 measures biological data in sensor 3 (S201), and controller causes communicator 34 to transmit the biological data to user terminal 2 (S202).

Next, when communicator 24 receives the biological data in user terminal 2, controller 21 causes communicator 24 to transmit the biological data to server 1 while associating the biological data with the user ID (S203).

Subsequently, when communicator 13 receives the biological data in server 1, data analyzer 111 compares the biological data with the normal range, and accumulates a determination result (S204). The determination result is accumulated in the "determination result" field of the record of the corresponding user in normal-range data table T2 while the user ID is allowed to serve as a key.

Next, when a predetermined period of time elapses, data analyzer 111 causes communicator 13 to transmit time-period information in which biogas concentration is less than the lower limit of the normal range in the predetermined period of time to user terminal 2 (S205).

Subsequently, when communicator 24 receives the time-period information in user terminal 2, controller 21 causes display 23 to display the time-period information (S206).

When the predetermined period of time does not elapse, processing after S205 is not performed, and S201 to S204 are repeated.

Figure 14:
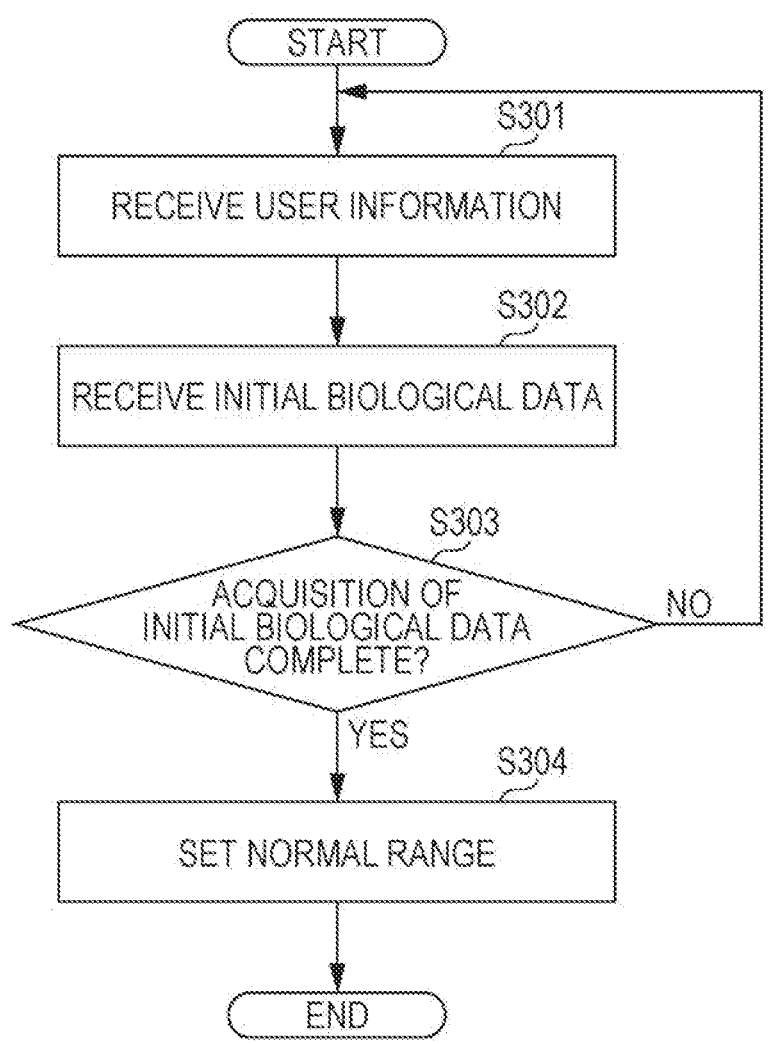
FIG. 14 is a flowchart illustrating detailed processing in an initial phase according to the first embodiment of the present disclosure.

FIG. 14 is a flowchart illustrating detailed processing in an initial phase according to the first embodiment of the present disclosure. This flowchart is performed by server 1. First, communicator 13 receives user information transmitted from user terminal 2 (S301).

Next, communicator 13 receives initial biological data transmitted from user terminal 2 (S302). Subsequently, when the initial biological data has not been acquired (NO in S303), data analyzer 111 returns processing to S302. Meanwhile, when the initial biological data has been acquired (YES in S303), data analyzer 111 allows the processing to proceed to S304. Then, data analyzer 111 may complete acquisition of the initial biological data when the amount of the received initial biological data reaches a predetermined amount enough to calculate a normal range, or when a predetermined measurement period of time elapses after measurement of the initial biological data is started. In the present disclosure, depending on a measurement interval of biological data, one hour, two hours, three hours, . . . , one day, two days, three days, or the like is used as a measurement period of time in the initial phases, for example. When a measurement interval of biological data is short, for example, a large amount of initial biological data can be acquired in a short time. Accordingly, a measurement period of time of the initial biological data is shortened. When one hour is used as a measurement interval of biological data, for example, half a day, one day, two days, three days, or the like is used as a measurement period of time of initial biological data, for example. When one minute or one second is used as the measurement interval of biological data, ten minutes, twenty minute, one hour, two hours, three hours, or the like can be used initial biological data can be used as the measurement period of time of initial biological data, for example. However, these numeric values are only an example, and may be appropriately changed.

The measurement period of time of initial biological data corresponds to an example of the predetermined period of time.

Next, data analyzer 111 sets a normal range using the initial biological data acquired (S304). For example, it is assumed that initial biological data as shown in FIG. 6A is acquired. In this case, data analyzer 111 analyzes the initial biological data acquired to extract an upper limit peak and a lower limit peak of biogas concentration. Then, data analyzer 111 may calculate a value as upper limit DH by adding a predetermined margin to the upper limit peak, and a value as lower limit DL by subtracting the predetermined margin from the lower limit peak. Alternatively, data analyzer 111 may calculate a value as upper limit DH by adding a predetermined margin to an average value of upper peaks, and a value as lower limit DL by subtracting the predetermined margin from an average value of lower peaks. As described above, a normal range for each user is set.

Figure 15:
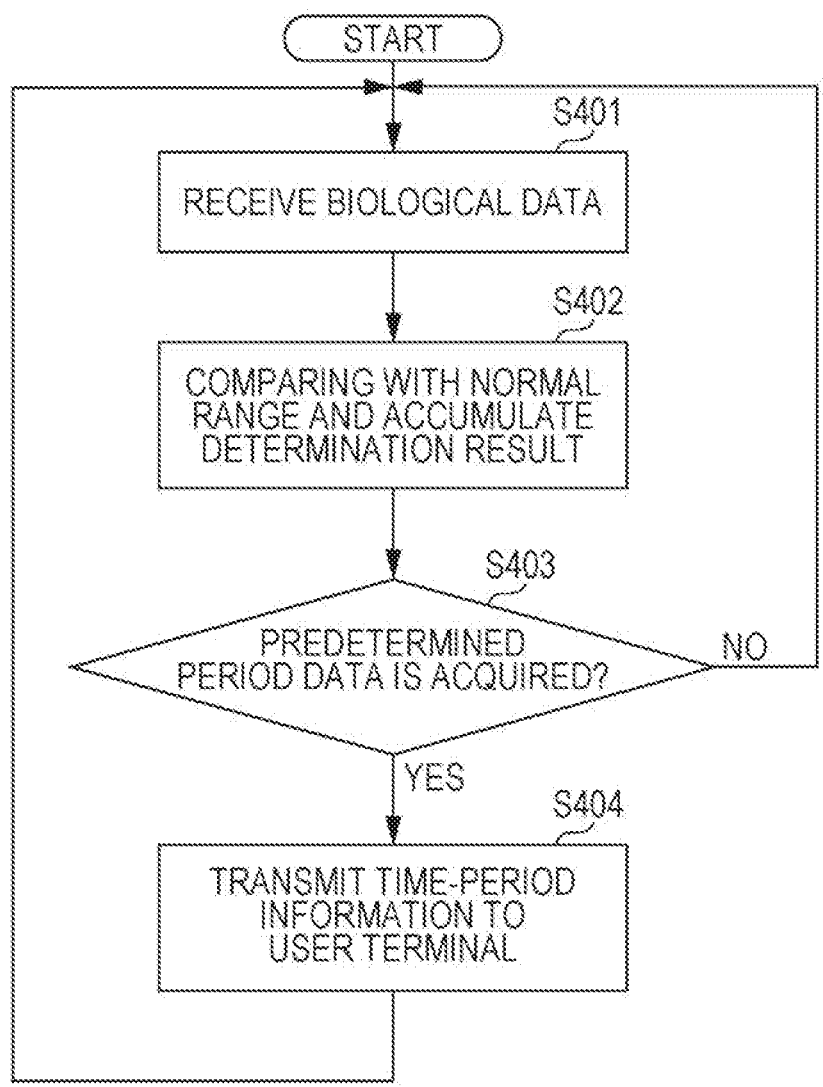
FIG. 15 is a flowchart illustrating detailed processing in a normal phase according to the first embodiment of the present disclosure.

FIG. 15 is a flowchart illustrating detailed processing in the normal phases according to the first embodiment of the present disclosure. The flowchart of FIG. 15 is periodically performed by server 1 at a measurement interval of biological data with sensor 3.

First, communicator 13 receives biological data from user terminal 2 (S401). Next, data analyzer 111 compares biogas concentration indicated by the biological data with the normal range of the corresponding user to determine whether a stress state is normal or abnormal, and accumulates a determination result in biological data table T4 (S402). Specifically; data analyzer 111 may store the determination result in biological data table T4 while associating the determination result with a user ID, a measurement date, and a biogas concentration. Refer to Biological data table T4 in FIG. 12. In the record in the first line, "2017.2.15" is described in the "date" field, and "10:00-11:00" is described in the "time" field. This is because the measurement interval of biological data was set at one hour, and the biological data was measured between ten o'clock and eleven o'clock on Feb. 15, 2017.

In the present disclosure, 2-ethylhexanoic acid is used as biogas to be measured. 2-ethylhexanoic acid has a negative correlation with a level of stress. Thus, data analyzer 111 may determine that a stress state is abnormal when a biogas concentration is less than lower limit DL of the normal range, and determine that the stress state is normal when the biogas concentration is equal to or more than lower limit DL.

Next, when biological data for the predetermined period of time (e.g., for one day) is acquired (YES in S403), data analyzer 111 allows processing to proceed to S404. When the biological data for one day is not acquired (NO in S403), data analyzer 111 returns the processing to S401, and acquires biological data measured next.

Using one day as the predetermined period of time may allow data analyzer 111 to determine YES in S403, when "0:00" appears in the "time" field, and then biological data for one day acquired in the previous day may be treated as biological data on a processing object.

Next, data analyzer 111 transmits time-period information to a user terminal using communicator 13 (S404). Data analyzer 111 here may transmit the time-period information while including data indicating temporal transition of biogas concentration acquired in the predetermined period of time, and a time period out of the normal range, in the time-period information. As timing of transmitting the time-period information, a predetermined time in the next morning (e.g., seven o'clock) may be used, for example. When S404 is finished, the processing returns to S401.

As described above, it is determined whether stress is less than the normal range.

Time Period Information

Figure 16:
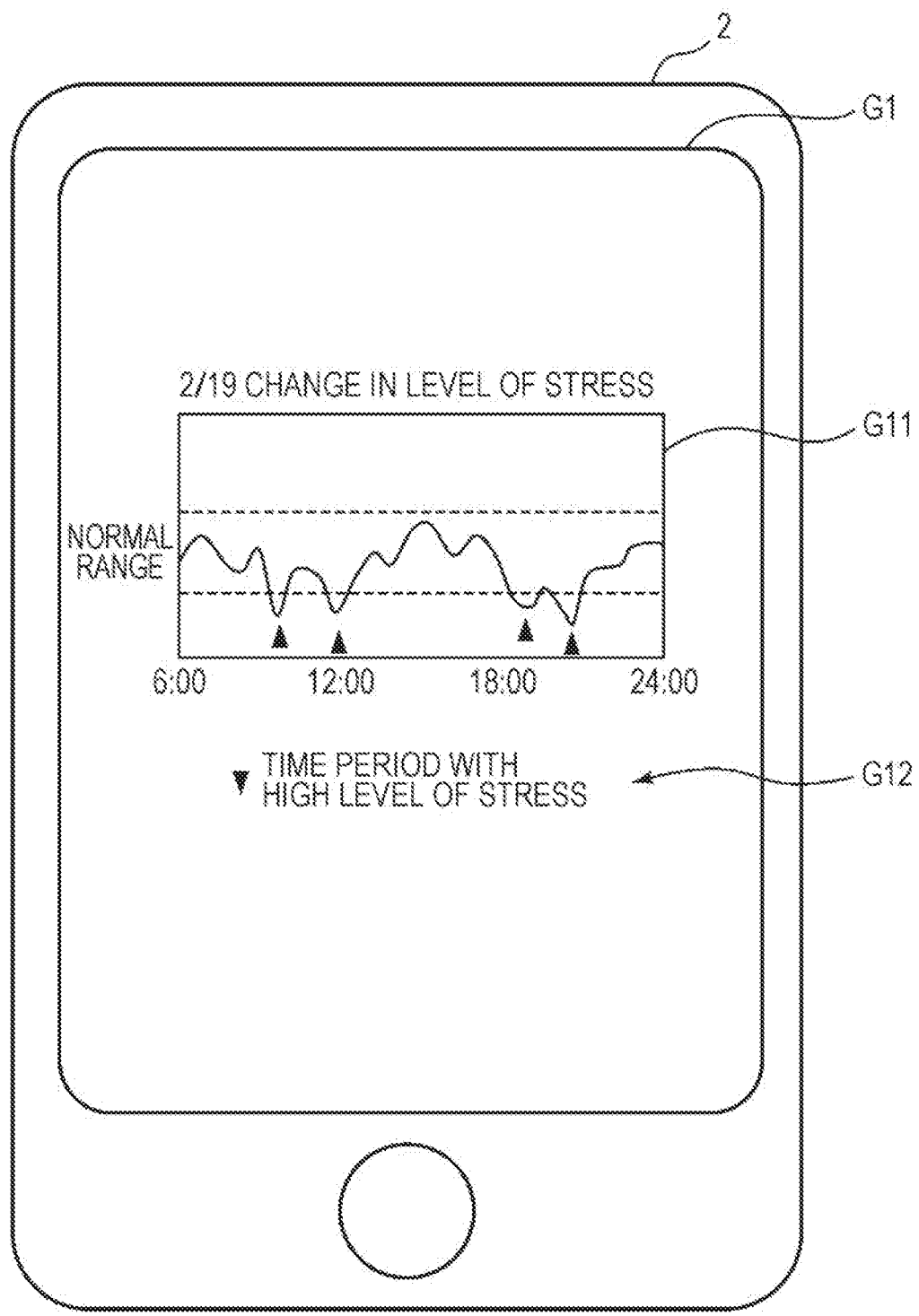
FIG. 16 illustrates an example of a display screen displayed in a user terminal as time-period information.

FIG. 16 illustrates an example of display screen G1 displayed in user terminal 2 as time-period information. Display screen G1 includes graph G11 and message display section G12.

Graph G11 shows temporal transition of a level of stress in biological data acquired in the predetermined period of time (here, one day of February 19). In graph G11, the vertical axis represents a level of stress, and the horizontal axis represents time. The level of stress corresponds to a correlation to biogas concentration. In graph G11, a triangular marker is displayed at each place with a level of stress less than the lower limit of the normal range. In this way, a time period in which biogas concentration is less than the lower limit of the normal range is shown to a user. This enables the user to find out a cause (stressor) of increase in stress by recalling life of the user itself in the predetermined period of time.

Message display section G12 displays a message for notifying a user that the triangular marker is a time period with a high level of stress.

Schedule Information

Display screen G1 illustrated in FIG. 16 may display schedule information on a corresponding user. In this case, server 1 may include a database for managing schedule information on a user.

The database for managing the schedule information stores information items such as a "user ID", a "schedule", and a "date", for example, while associating them with each other. The "schedule" is an action schedule (e.g., a "conference", etc.) of a user, and is received by the user with user terminal 2, for example. The "date" is a scheduled date in which the action schedule described in the "schedule" is taken, and is received by the user with user terminal 2.

When transmitting time-period information, server 1 transmits the time-period information to user terminal 2 while including schedule information on a corresponding user in a predetermined period of time in the time-period information.

User terminal 2 may generate display screen G1 using the schedule information. The schedule information may be displayed in a display mode in which schedule information on a user is displayed in graph G11 while being associated with a time period. For example, an aspect of displaying the schedule of the user while the schedule is associated with time indicated in graph G11 may be used. This enables the user to easily find out a cause and effect relationship between stress and action of the user itself.

As described above, in the first embodiment, the amount of stress is objectively determined using 2-ethylhexanoic acid, which is biogas estimated to have a relationship with stress. This enables a cumulative level of stress to be objectively grasped without being affected by subjective feeling of a person.

In the first embodiment, user terminal 2 displays a time period in which a concentration of 2-ethylhexanoic acid of the user is less than the lower limit of the normal range to enable a user to objectively grasp how much the amount of stress was felt in a day by recalling the day, for example. In addition, in the first embodiment, a stressor of the user can be found out with a clue of an incident which has occurred to the user in the time period in which a concentration of 2-ethylhexanoic acid of the user was less than the lower limit of the normal range.

Second Embodiment

Figure 17:
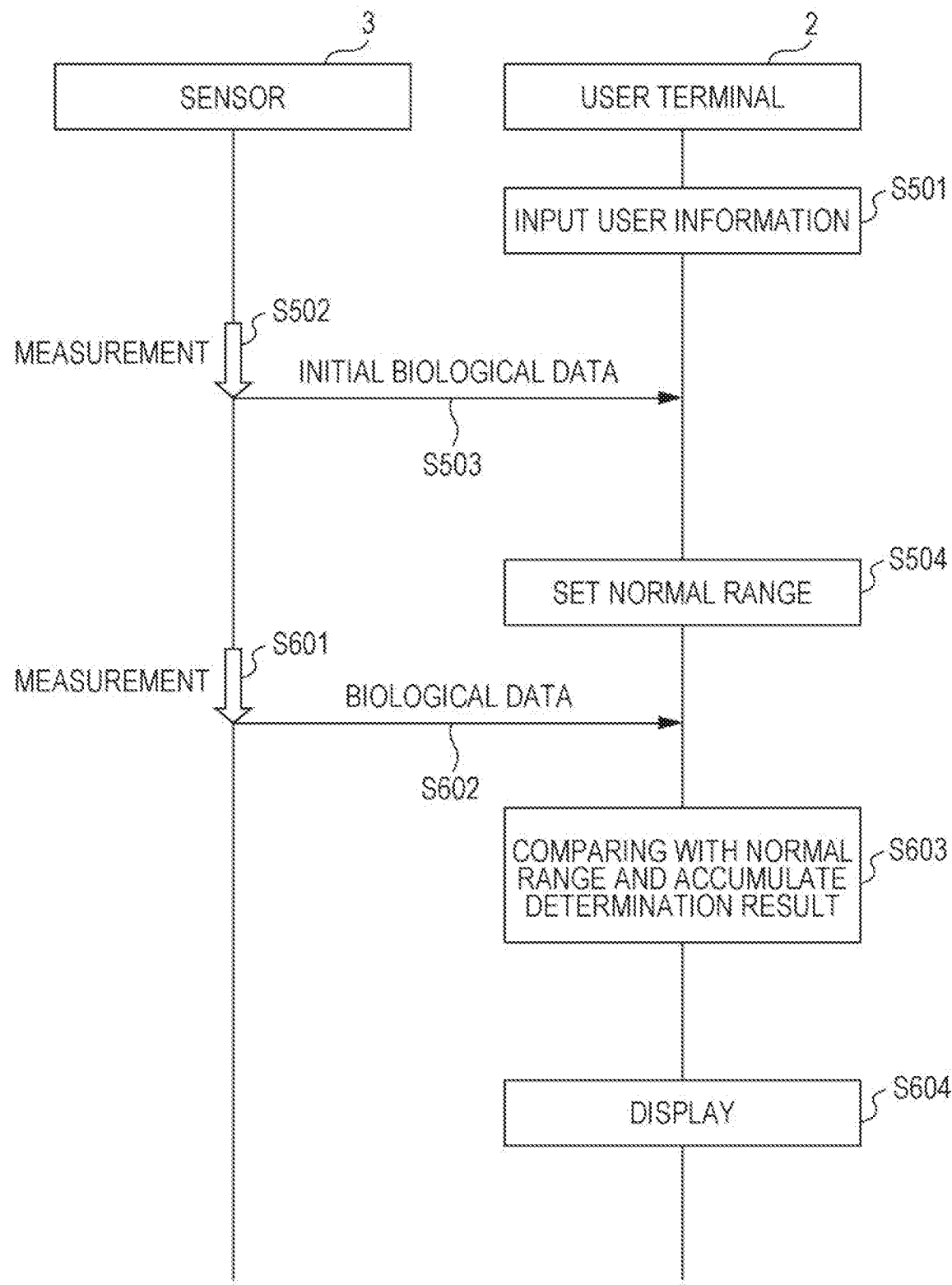
FIG. 17 is a sequence diagram illustrating processing of an information processing system according to a second embodiment the present disclosure.

Second embodiment includes user terminal 2 into which functions of server 1 are incorporated. In the second embodiment, the component same as that in the first embodiment is designated by the same reference sign to eliminate duplicated description. FIG. 17 is a sequence diagram illustrating processing of an information processing system according to the second embodiment the present disclosure.

FIG. 17 is different from FIG. 13 in that server 1 is eliminated and the information processing system includes sensor 3 and user terminal 2. S501 to S504 correspond to the initial phases.

S501, S502, and S503 are identical to S101, S103, and S104, in FIG. 13, respectively. S504 is identical to S106 in FIG. 13 except for a processing subject that is not sever 1 but user terminal 2.

S601 to S604 correspond to the normal phases. S601 and S602 are identical to S201 and S202 in FIG. 13, respectively. S603 is identical to S204 in FIG. 13 except for a processing subject that is not sever 1 but user terminal 2.

In S604, when a determination result in S603 is abnormal, controller 21 of user terminal 2 causes display 23 to display information indicating stress on a user that is out of the normal range. Meanwhile, in S604, when the determination result in S603 is normal, controller 21 of user terminal 2 causes display 23 to display information indicating stress on the user that is within the normal range.

Figure 18:
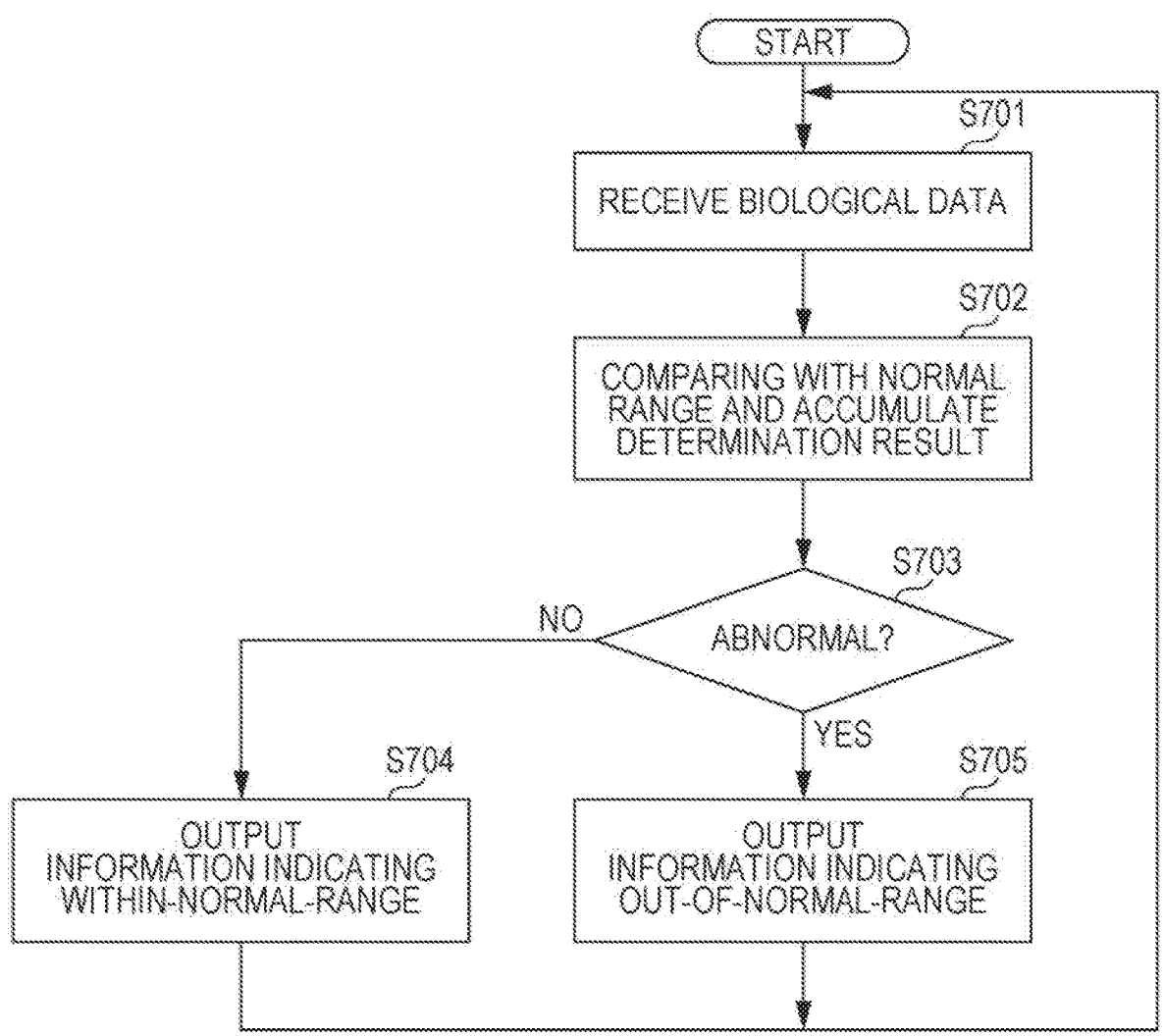
FIG. 18 is a flowchart illustrating detailed processing in a normal phase according to the second embodiment of the present disclosure.

In the second embodiment, a flowchart of the initial phases is identical to that of FIG. 14. FIG. 18 is a flowchart illustrating detailed processing in the normal phases according to the second embodiment of the present disclosure. This flowchart is performed by user terminal 2.

First, communicator 24 receives biological data from sensor 3 (3701). Next, controller 21 compares biogas concentration indicated by the biological data with the normal range of the corresponding user to determine whether a stress state is normal or anomaly, and accumulates a determination result in biological data table T4 (S702).

Next, when a determination result in S703 is abnormal (YES in S703), controller 21 causes display 23 to display information indicating that a level of stress (biogas concentration) is out of the normal range. As the information indicating that a level of stress is out of the normal range, a message such as "stress is high" may be used, for example.

Meanwhile, when the determination result in S703 is not abnormal, i.e., is normal (NO in S703), controller 21 causes display 23 to display information indicating that a level of stress (biogas concentration) is within the normal range. As the information indicating that a level of stress is within the normal range, a message such as "stress is normal" may be used, for example.

When S704 and S705 are finished, the processing returns to S701.

As described above, the information processing system according to the second embodiment is configured to cause display 23 to display information indicating whether a level of stress is within the normal range, so that a result of objective determination whether a user is in a stress state at present can be notified to the user.

The present disclosure is allowed to apply modifications below.

Figure 19:
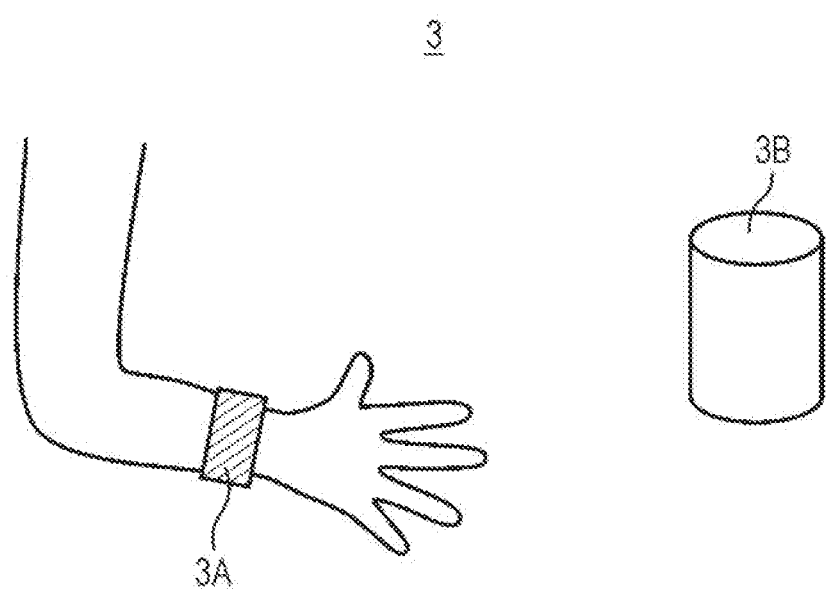
FIG. 19 illustrates an example of sensor 3 according to a modification of the present disclosure.

(1) While sensor 3 is integrally formed in the description above, the present disclosure is not limited to this. FIG. 19 illustrates an example of sensor 3 according to a modification of the present disclosure. Sensor 3 according to the modification includes wearable part 3A to be worn by a user and body part 3B that are separated from each other. Wearable part 3A is composed of a wearable band that is detachable from the wrist of a user. Wearable part 3A is provided with absorbent that absorbs biogas.

Wearable part 3A is configured to be detachable from body part 3B as well. Body part 3B comprises detector 33, controller 31, and communicator 34, illustrated in FIG. 7. When wearable part 3A is worn, body part 3B separates biogas from the absorbent by heating the absorbent with a heater, for example, and analyzes the biogas to extract biogas to be measured (here, 2-ethylhexanoic acid), thereby measuring a biogas concentration of the biogas to be measured. Then, body part 3B transmits biological data including the biogas concentration measured to user terminal 2. In the modification, wearable part 3A is reduced in size to enable reduction in burden of a user.

(2) In the second embodiment, user terminal 2 may be composed of a computer that is used by a doctor who examines a user. In this case, the doctor may allow the user to wear sensor 3 during an examination for allowing user terminal 2 to acquire biological data, and allow user terminal 2 to determine stress on the user.

Alternatively, the doctor may allow user terminal 2 to determine stress on the user by allowing user terminal 2 to acquire biological data that is preliminarily measured by sensor 3 for a predetermined period of time (e.g., one day, two days, or three days). In this case, the user is preliminarily instructed by the doctor to wear sensor 3. Sensor 3 stores the biological data measured in the predetermined period of time in memory 32 while associating the biological data with measurement time. Memory 32 is here detachable from sensor 3.

The user brings the memory 32 when visiting a hospital. The doctor connects this memory 32 to user terminal 2 to cause user terminal 2 to acquire the biological data acquired in the predetermined period of time. When biogas concentration indicated by the biological data acquired is less than the lower limit of the normal range, user terminal 2 allows display 23 to display information indicating that fact. Meanwhile, when the biogas concentration indicated by the biological data acquired is equal to or less than the upper limit of the normal range, user terminal 2 allows display 23 to display information indicating that fact.

This modification enables useful data for preventing a mental disorder to be provided to a doctor who examines a user visiting a hospital. This modification may be applied to periodical health examination.

INDUSTRIAL APPLICABILITY

The present disclosure is expected to be capable of preventing a mental disorder of a user, and thus is useful for an information processing system of managing stress on the user.

REFERENCE SIGNS LIST 1 server
2 user terminal
3 sensor
11 controller
12 memory
13 communicator
21 controller
22 memory
23 display
24 communicator
31 controller
32 memory
33 detector
34 communicator
111 data analyzer
NT network
T2 normal-range data table
T4 biological data table
U1 user

The invention claimed is:

1. A method for providing information in an information processing system, the method comprising:
    acquiring, via a network, biogas information at multiple timings and time information corresponding to each of the multiple timings, wherein the biogas information represents a concentration of 2-ethylhexanoic acid of a user acquired by a sensor that detects the 2-ethylhexanoic acid discharged from a skin surface of the user;
    obtaining reference information representing a lower limit of a normal range of the concentration of 2-ethylhexanoic acid per unit period of time, using a memory storing the reference information representing the lower limit of the normal range;
    determining a stress time period during which a concentration of the 2-ethylhexanoic acid of the user is less than the lower limit of the normal range, based on the acquired biogas information; and
    outputting time period information indicating the determined stress time period to an information terminal of the user, to display the stress time period indicated by the time period information on a display of the information terminal.

2. The method according to claim 1, wherein
the lower limit of the normal range of the concentration of 2-ethylhexanoic acid per unit period of time is set for the user as individual information of the user, based on the biogas information acquired in a predetermined period of time.

3. The method according to claim 1, wherein
the lower limit of the normal range of the concentration of 2-ethylhexanoic acid per unit period of time is used commonly to a plurality of users including the user.

4. The method according to claim 1, wherein
the stress time period indicated by the time period information is displayed in association with schedule information on the user, on the information terminal.

5. The method according to claim 1, wherein
the sensor for detecting 2-ethylhexanoic acid is built in a device to be worn on an arm of the user.

6. The method according to claim 1, wherein
the time information corresponding to each of the multiple timings is associated with each time when the sensor detects the biogas.

7. An information processing system comprising:
a server device; and
an information terminal,
wherein the server device is configured to:
    acquire, via a network, biogas information at multiple timings and time information corresponding to time at each of the multiple timings, wherein the biogas information represents a concentration of 2-ethylhexanoic acid of a user acquired by a sensor that detects the 2-ethylhexanoic acid discharged from a skin surface of the user;
    obtain reference information representing a lower limit of a normal range of the concentration of 2-ethylhexanoic acid per unit period of time, using a memory storing the reference information representing the lower limit of the normal range;
    determine a stress time period during which a concentration of the 2-ethylhexanoic acid of the user is less than the lower limit of the normal range, based on the acquired biogas information; and
    output time period information indicating the determined stress time period to the information terminal, and
wherein the information terminal displays the stress time period indicated by the time period information, on a display of the information terminal.

8. An information terminal comprising:
a display operatively connected to a server device,
wherein the server device is configured to:
    acquire, via a network, biogas information at multiple timings and time information corresponding to time at each of the multiple timings, wherein the biogas information represents a concentration of 2-ethylhexanoic acid of a user acquired by a sensor that detects the 2-ethylhexanoic acid discharged from a skin surface of the user;
    obtain reference information representing a lower limit of a normal range of the concentration of 2-ethylhexanoic acid per unit period of time, using a memory storing the reference information representing the lower limit of the normal range;
    determine a stress time period during which a concentration of the 2-ethylhexanoic acid of the user is less than the lower limit of the normal range, based on the acquired biogas information; and
    output time period information indicating the determined stress time period to the information terminal, and
wherein the display displays the stress time period indicated by the time period information.

9. A method for processing information using a computer, the method comprising:
    acquiring, via a network, biogas information at multiple timings and time information corresponding to time at each of the multiple timings, wherein the biogas information represents a concentration of 2-ethylhexanoic acid of a user acquired by a sensor that detects the 2-ethylhexanoic acid discharged from a skin surface of the user;
    obtaining reference information representing a lower limit of a normal range of the concentration of 2-ethylhexanoic acid per unit period of time, using a memory storing the reference information representing the lower limit of the normal range;
    determining a stress time period during which a concentration of the 2-ethylhexanoic acid of the user is less than the lower limit of the normal range, based on the acquired biogas information; and
    outputting notice information representing that stress on the user is less than a lower limit of a predetermined normal range within the determined stress time period to display the notice information on a display.

10. The method according to claim 9, wherein
the display is provided in an information terminal of the user.

* * * * *